US010813885B1

(12) United States Patent
Allphin et al.

(10) Patent No.: US 10,813,885 B1
(45) Date of Patent: *Oct. 27, 2020

(54) CONTROLLED RELEASE DOSAGE FORMS FOR HIGH DOSE, WATER SOLUBLE AND HYGROSCOPIC DRUG SUBSTANCES

(71) Applicant: JAZZ PHARMACEUTICALS, INC., Palo Alto, CA (US)

(72) Inventors: Clark Allphin, Seattle, WA (US); James Pfeiffer, Palo Alto, CA (US)

(73) Assignee: JAZZ PHARMACEUTICALS, INC., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/916,677

(22) Filed: Jun. 30, 2020

Related U.S. Application Data

(63) Continuation of application No. 16/712,260, filed on Dec. 12, 2019, which is a continuation of application No. 16/025,487, filed on Jul. 2, 2018, now Pat. No. 10,758,488, which is a continuation of application No. 13/071,369, filed on Mar. 24, 2011, now abandoned.

(60) Provisional application No. 61/317,212, filed on Mar. 24, 2010.

(51) Int. Cl.
*A61K 9/20* (2006.01)
*A61K 31/19* (2006.01)
*A61K 9/28* (2006.01)
*A61K 9/24* (2006.01)

(52) U.S. Cl.
CPC ............ *A61K 9/2054* (2013.01); *A61K 9/209* (2013.01); *A61K 9/284* (2013.01); *A61K 9/286* (2013.01); *A61K 9/2833* (2013.01); *A61K 9/2846* (2013.01); *A61K 9/2853* (2013.01); *A61K 9/2866* (2013.01); *A61K 9/2893* (2013.01); *A61K 31/19* (2013.01)

(58) Field of Classification Search
None
See application file for complete search history.

(56) References Cited

U.S. PATENT DOCUMENTS

| | | |
|---|---|---|
| 3,051,619 A | 8/1962 | Laborit |
| 3,419,588 A | 12/1968 | De Man |
| 4,221,778 A | 9/1980 | Raghunathan |
| 4,374,441 A | 2/1983 | Carter et al. |
| 4,393,236 A | 7/1983 | Klosa |
| 4,510,128 A | 4/1985 | Khanna |
| 4,524,217 A | 6/1985 | Davenport et al. |
| 4,687,662 A | 8/1987 | Schobel |
| 4,738,985 A | 4/1988 | Kluger et al. |
| 4,916,161 A | 4/1990 | Patell |
| 4,939,949 A | 7/1990 | Langenberg |
| 4,983,632 A | 1/1991 | Gessa et al. |
| 5,294,430 A | 3/1994 | Borch et al. |
| 5,380,937 A | 1/1995 | Koehler et al. |
| 5,415,870 A | 5/1995 | Gergely et al. |
| 5,594,030 A | 1/1997 | Conte et al. |
| 5,753,708 A | 5/1998 | Koehler et al. |
| 5,758,095 A | 5/1998 | Albaum et al. |
| 5,833,599 A | 11/1998 | Schrier et al. |
| 5,840,331 A | 11/1998 | Van Cauter et al. |
| 5,845,255 A | 12/1998 | Mayuad |
| 5,955,106 A | 9/1999 | Moeckel et al. |
| 5,990,162 A | 11/1999 | Scharf |
| 6,014,631 A | 1/2000 | Teagarden et al. |
| 6,022,562 A | 2/2000 | Autant et al. |
| 6,067,524 A | 5/2000 | Byerly et al. |
| 6,112,182 A | 8/2000 | Akers et al. |
| 6,317,719 B1 | 11/2001 | Schrier et al. |
| 6,322,819 B1 | 11/2001 | Burnside et al. |
| 6,356,873 B1 | 3/2002 | Teagarden et al. |
| 6,384,020 B1 | 5/2002 | Flanner et al. |
| 6,436,998 B1 | 8/2002 | Cacciaglia et al. |
| 6,472,431 B2 | 10/2002 | Cook et al. |
| 6,472,432 B1 | 10/2002 | Perricone |
| 6,565,872 B2 | 5/2003 | Wu et al. |
| 6,780,889 B2 | 8/2004 | Cook et al. |
| 7,072,840 B1 | 7/2006 | Mayuad |
| 7,262,219 B2 | 8/2007 | Cook et al. |
| 7,568,822 B2 | 8/2009 | Ibrahim |
| 7,668,730 B2 | 2/2010 | Reardan et al. |

(Continued)

FOREIGN PATENT DOCUMENTS

| | | |
|---|---|---|
| CA | 2 112 663 C | 4/2002 |
| CN | 102905688 A | 1/2013 |

(Continued)

OTHER PUBLICATIONS

"Hib-Imune," Physicians Desk Reference (41st ed.), (1987), 1095-1096.
"HibVAX," Physicians Desk Reference (41st ed.), (1987), 870.
"Malic Acid," The Handbook of Pharmaceutical Excipients, 2nd Ed., (1994 ), pp. 285-286, 633.
"Phospholine Iodide," Physicians Desk Reference (50th ed.), (1996), 2784.
"Taxotere," Physicians Desk Reference (51st ed.), (1997), 2204-2207.
21 C.F.R. 184, Food and Drug Administration, HHS, (1998), pp. 441-535.

(Continued)

*Primary Examiner* — Patricia Duffy
*Assistant Examiner* — Garen Gotfredson
(74) *Attorney, Agent, or Firm* — Cooley LLP

(57) ABSTRACT

Controlled release dosage forms are described herein. The controlled release formulations described herein provide prolonged delivery of high dose drugs that are highly water soluble and highly hygroscopic. In specific embodiments, controlled release dosage forms for delivery of a drug selected from GHB and pharmaceutically acceptable salts, hydrates, tautomers, solvates and complexes of GHB. The controlled release dosage forms described herein may incorporate both controlled release and immediate release formulations in a single unit dosage form.

15 Claims, 9 Drawing Sheets

(56) References Cited

U.S. PATENT DOCUMENTS

| | | |
|---|---|---|
| 7,765,106 B2 | 7/2010 | Reardan et al. |
| 7,765,107 B2 | 7/2010 | Reardan et al. |
| 7,797,171 B2 | 9/2010 | Reardan et al. |
| 7,851,506 B2 | 12/2010 | Cook et al. |
| 7,895,059 B2 | 2/2011 | Reardan et al. |
| 8,101,209 B2 | 1/2012 | Legrand et al. |
| 8,193,211 B2 | 6/2012 | Liang et al. |
| 8,202,537 B2 | 6/2012 | Mehta et al. |
| 8,263,125 B2 | 9/2012 | Vaya et al. |
| 8,263,650 B2 | 9/2012 | Cook et al. |
| 8,324,275 B2 | 12/2012 | Cook et al. |
| 8,457,988 B1 | 6/2013 | Reardan et al. |
| 8,461,197 B2 | 6/2013 | Tung |
| 8,461,203 B2 | 6/2013 | Cook et al. |
| 8,529,954 B2 | 9/2013 | Lebon et al. |
| 8,589,182 B1 | 11/2013 | Reardan et al. |
| 8,591,922 B1 | 11/2013 | Allphin et al. |
| 8,598,191 B2 | 12/2013 | Liang et al. |
| 8,680,228 B2 | 3/2014 | Guo et al. |
| 8,731,963 B1 | 5/2014 | Reardan et al. |
| 8,759,394 B2 | 6/2014 | Tung et al. |
| 8,771,735 B2 | 7/2014 | Rourke et al. |
| 8,772,306 B1 | 7/2014 | Eller |
| 8,778,301 B2 | 7/2014 | Mamelak et al. |
| 8,778,398 B2 | 7/2014 | Rourke et al. |
| 8,859,619 B2 | 10/2014 | Cook et al. |
| 8,901,173 B2 | 12/2014 | Allphin et al. |
| 8,952,062 B2 | 2/2015 | Cook et al. |
| 9,132,107 B2 | 9/2015 | Allphin et al. |
| 9,555,017 B2 | 1/2017 | Allphin et al. |
| 9,770,514 B2 | 9/2017 | Ghebre-Sellassie |
| 9,795,567 B2 | 10/2017 | Rourke et al. |
| 10,195,168 B2 | 2/2019 | Allphin et al. |
| 10,272,062 B2 | 4/2019 | Mégret et al. |
| 10,398,662 B1 | 9/2019 | Allphin et al. |
| 2003/0180249 A1 | 9/2003 | Khanna et al. |
| 2004/0092455 A1 | 5/2004 | Mamelak et al. |
| 2005/0031688 A1 | 2/2005 | Ayala |
| 2005/0037077 A1 | 2/2005 | Legrand et al. |
| 2005/0142192 A1 | 6/2005 | Benjamin et al. |
| 2006/0018933 A1 | 1/2006 | Vaya et al. |
| 2006/0024365 A1 | 2/2006 | Vaya et al. |
| 2006/0069040 A1 | 3/2006 | Mamelak |
| 2006/0210630 A1 | 9/2006 | Liang et al. |
| 2007/0270491 A1 | 11/2007 | Cook et al. |
| 2008/0003267 A1 | 1/2008 | Spencer et al. |
| 2008/0069871 A1 | 3/2008 | Vaughn et al. |
| 2008/0085304 A1 | 4/2008 | Baichwal et al. |
| 2008/0118571 A1 | 5/2008 | Lee et al. |
| 2008/0226564 A1 | 9/2008 | Weers et al. |
| 2008/0292700 A1 | 11/2008 | Nghiem et al. |
| 2008/0293698 A1 | 11/2008 | Johnson |
| 2009/0137565 A1 | 5/2009 | Frucht |
| 2009/0155357 A1 | 6/2009 | Muhuri |
| 2009/0317355 A1 | 12/2009 | Roth et al. |
| 2010/0112056 A1 | 5/2010 | Rourke et al. |
| 2011/0039929 A1 | 2/2011 | Cook et al. |
| 2011/0111027 A1 | 5/2011 | Rourke et al. |
| 2012/0020833 A1 | 1/2012 | Cook et al. |
| 2012/0076865 A1 | 3/2012 | Allphin et al. |
| 2012/0148672 A1 | 6/2012 | Mehta et al. |
| 2012/0202879 A1 | 8/2012 | Cook et al. |
| 2012/0202880 A1 | 8/2012 | Cook et al. |
| 2013/0230587 A1 | 9/2013 | Pilgaonkar et al. |
| 2013/0273159 A1 | 10/2013 | Howard et al. |
| 2014/0004202 A1 | 1/2014 | Suplie et al. |
| 2014/0037745 A1 | 2/2014 | Liang et al. |
| 2014/0093578 A1 | 4/2014 | Mehta et al. |
| 2014/0127306 A1 | 5/2014 | Mehta et al. |
| 2014/0171506 A1 | 6/2014 | Allphin et al. |
| 2014/0271896 A1 | 9/2014 | Abu Shmeis et al. |
| 2014/0348917 A1 | 11/2014 | Rourke et al. |
| 2015/0005334 A1 | 1/2015 | Shah et al. |
| 2015/0073052 A1 | 3/2015 | Cook et al. |
| 2016/0068463 A1 | 3/2016 | Peoples et al. |
| 2016/0228379 A1 | 8/2016 | Kumar et al. |
| 2016/0271070 A1 | 9/2016 | Singh et al. |
| 2016/0346200 A1 | 12/2016 | Sommer et al. |
| 2016/0346216 A1 | 12/2016 | Chen |
| 2017/0119627 A1 | 5/2017 | Bhargava et al. |
| 2017/0340519 A9 | 11/2017 | Bhargava et al. |
| 2018/0008539 A1 | 1/2018 | Singh et al. |
| 2018/0021284 A1 | 1/2018 | Mégret et al. |
| 2018/0318222 A1 | 11/2018 | Allphin et al. |
| 2020/0113840 A1 | 4/2020 | Allphin et al. |

FOREIGN PATENT DOCUMENTS

| | | |
|---|---|---|
| CN | 102958930 A | 3/2013 |
| CN | 103209966 A | 7/2013 |
| CN | 103209967 A | 7/2013 |
| EP | 0203768 A2 | 12/1986 |
| EP | 0235408 A1 | 9/1987 |
| EP | 0344704 A1 | 12/1989 |
| EP | 0616804 A1 | 9/1994 |
| EP | 0635265 A1 | 1/1995 |
| EP | 0635265 B1 | 2/2000 |
| EP | 1140061 A2 | 10/2001 |
| EP | 1316309 A1 | 6/2003 |
| EP | 2760911 B1 | 11/2017 |
| GB | 922029 A | 3/1963 |
| GB | 2295390 A | 5/1996 |
| JP | S57-042651 A | 3/1982 |
| JP | 62-12715 A | 1/1987 |
| JP | 04-049212 A | 2/1992 |
| JP | 05-508422 A | 11/1993 |
| JP | H06-508839 A | 10/1994 |
| JP | 7-53365 A | 2/1995 |
| JP | H8-511257 A | 11/1996 |
| JP | 09-104620 A | 4/1997 |
| JP | H10-505604 A | 6/1998 |
| JP | 2001-513552 A | 9/2001 |
| JP | 2004-514732 A | 5/2004 |
| JP | 2007-521231 A | 8/2007 |
| JP | 2008-512386 A | 4/2008 |
| JP | 2008-519847 A | 6/2008 |
| JP | 2008-528571 A | 7/2008 |
| JP | 2009-532331 A | 9/2009 |
| JP | 2011-500865 A | 1/2011 |
| RU | 2210360 C1 | 8/2003 |
| WO | WO 1994/028880 A1 | 12/1994 |
| WO | WO 1996/040105 A1 | 12/1996 |
| WO | WO 1999/009972 A1 | 3/1999 |
| WO | WO 2000/038672 A2 | 7/2000 |
| WO | WO 2002/045684 A2 | 6/2002 |
| WO | WO 2005/016318 A1 | 2/2005 |
| WO | WO 2005/099671 A2 | 10/2005 |
| WO | WO 2006/029155 A2 | 3/2006 |
| WO | WO 2006/053186 A2 | 5/2006 |
| WO | WO 2006/080029 A1 | 8/2006 |
| WO | WO 2007/053698 A2 | 5/2007 |
| WO | WO 2007/103200 A2 | 9/2007 |
| WO | WO 2008/086804 A2 | 7/2008 |
| WO | WO 2009/056550 A2 | 5/2009 |
| WO | WO 2010/053691 A1 | 5/2010 |
| WO | WO 2011/119839 A1 | 9/2011 |
| WO | WO 2011/127252 A2 | 10/2011 |
| WO | WO 2011/135461 A2 | 11/2011 |
| WO | WO 2011/139271 A1 | 11/2011 |
| WO | WO 2011/140310 A2 | 11/2011 |
| WO | WO 2012/028688 A1 | 3/2012 |
| WO | WO 2012/107652 A2 | 8/2012 |
| WO | WO 2014/078014 A2 | 5/2014 |
| WO | WO 2015/120006 A1 | 8/2015 |
| WO | WO 2015/120110 A2 | 8/2015 |
| WO | WO 2016/087952 A1 | 6/2016 |
| WO | WO 2016/178132 A1 | 10/2016 |
| WO | WO 2015/166473 A1 | 3/2017 |
| WO | WO 2017/147375 A1 | 8/2017 |

(56) References Cited

FOREIGN PATENT DOCUMENTS

| WO | WO 2017/182851 A1 | 10/2017 |
|---|---|---|
| WO | WO 2018/015563 A1 | 1/2018 |

OTHER PUBLICATIONS

Activase, Physicians Desk Reference (50th ed.), (1996), pp. 312, 1058-1061.
Advisory Action dated Mar. 12, 2012 in co-pending U.S. Appl. No. 12/264,709, now US 2010/0112056.
Akifuddin et al. "Preparation, characterization and in-vitro evaluation of microcapsules for controlled release of Diltiazem hydrochloride by Ionotropic gelation technique." Journal of Applied Pharmaceutical Science (2013); 3.4: 35-42.
Amendment and Response, Under 37 C.F.R. § 1.11 and Record of Interview, filed Oct. 25, 2013, for U.S. Appl. No. 13/787,437, 8 pages.
Amendment filed Jul. 17, 2012 in U.S. Appl. No. 13/446,940.
Amendment to Response to filed May 1, 2014, for U.S. Appl. No. 13/787,437, 8 pages.
Amendment, filed Jan. 10, 2014, for U.S. Appl. No. 13/787,437, 8 pages.
Anal ("Controlled-Release Dosage Forms," Pharmaceutical Sciences Encyclopedia: Drug Discovery, Development, and Manufacturing (2010)).
Anand et al. "Ion-exchange resins: carrying drug delivery forward." Drug Discovery Today (2001); 6.17: 905-914.
Arena et al. "Absorption of sodium γ-hydroxybutyrate and its Prodrug γ-butyrolactone: Relationship between in vitro transport and in Vivo absorption." Journal of Pharmaceutical Sciences (1980); 69 (3): 356-358.
Australian Examination Report, dated Jan. 19, 2016, for Australian Patent Application No. 2010352575, 3 pages.
Australian Examination Report, dated Jul. 1, 2014, for Australian Patent Application No. 2010352575, 4 pages.
Australian Notice of Acceptance, dated Apr. 8, 2016, for Australian Patent Application No. 2010352575, 2 pages.
Australian Examination Report, dated Jun. 30, 2014, for Australian Patent Application No. 2011232408, 3 pages.
Australian Notice of Acceptance, dated Jul. 21, 2015, for Australian Patent Application No. 2011232408, 2 pages.
Bedard, "Nocturnal γ-Hydroxybutyrate—Effect on Periodic Leg Movements and Sleep Organization of Narcoleptic Patients," Clin Neuropharmacol., 12(1), Feb. 1989, 29-36.
Berner, Jon E., "A Case of Sodium Oxybate Treatment of Tardive Dyskinesia and Bipolar Disorder," J. Clin. Psychiatry, 2008, 69:5, p. 862.
Berthier, et al., "Possible Involvement of a Gamma-Hydroxybutyric Acid Receptor in Startle Disease," Acta Paediatr, 83, 1994, 678-680.
Borgen et al., "The influence of gender and food on the pharmacokinetics of sodium oxybate oral solution in healthy subjects." J Clin Pharmacol. (2003); 43(1): 59-65.
Borgen, L., et al. "Xyrem® (sodium oxybate): A Study of Dose Proportionality in Healthy Human Subjects." J. Clin. Pharmacol. (2000); 40: 1053.
Brazilian Office Action, dated Mar. 27, 2019, for Brazilian Patent Application No. BR112012024019-6, 4 pages.
Broughton et al., "The Treatment of Narcolepsy-Cataplexy with Nocturnal Gamma-Hydroxybutyrate." Can J. Neural Sci (1979); 6(1): 1-6.
Broughton, et al. "Effects of Nocturnal Gamma-Hydroxybutyrate on Spell/Waking Patterns in Narcolepsy-Cataplexy." Can J. Neural Sci (1980); 7 (1): 23-31.
Broughton, et al. "Gamma-Hydroxy-Butyrate in the Treatment of Narcolepsy: a Preliminary Report." (1976) Narcolepsy, Ny, N.Y., Spectrum Publications, Inc. 659-668.
Caballero et al. "Characterization of alginate beads loaded with ibuprofen lysine salt and optimization of the preparation method." International Journal of Pharmaceutics (2014); 460.1: 181-188.

Canadian Office Action, dated Dec. 22, 2015, for Canadian Patent Application No. 2,798,178, 3 pages.
Canadian Notice of Allowance, dated Oct. 25, 2016, for Canadian Patent Application No. 2,798,178, 1 page.
Canadian Office Action, dated Feb. 3, 2017, for Canadian Application No. 2,794,171, 4 pages.
Canadian Notice of Allowance, dated Oct. 31, 2017, for Canadian Patent Application No. 2,794,171, 1 page.
Canadian Office Action, dated Jul. 15, 2015, for Canadian Patent Application No. 2,740,146, 4 pages.
Canadian Office Action, dated Mar. 9, 2016, for Canadian Patent Application No. 2,740,146, 4 pages.
Canadian Office Action, dated May 10, 2016, for Canadian Patent Application No. 2,740,146, 4 pages.
Canadian Notice of Allowance, dated Mar. 7, 2017, for Canadian Patent Application No. 2,740,146, 1 page.
Chem Abstract ES302338, SciFinder®, (1964), 1 pg.
Chemical Abstracts: Seventh Collective Index, vols. 56-65, (1962-1966), 4 pgs.
Chinese Office Action, dated Apr. 14, 2014, for Chinese Patent Application No. 201080067754.9, 9 pages. (with English Translation).
Chinese Office Action, dated Aug. 28, 2013, for Chinese Patent Application No. 201080067754.9, 8 pages. (with English Translation).
Chinese Office Action, dated Dec. 1, 2014, for Chinese Patent Application No. 201080067754.9, 5 pages. (with English Translation).
Chinese Office Action, dated Aug. 4, 2015, for Chinese Patent Application No. 201080067754.9, 10 pages. (with English Translation).
Chinese Office Action, dated Dec. 26, 2014, for Chinese Patent Application No. 201180025543.3, 6 pages.
Chinese Office Action, dated May 29, 2014, for Chinese Patent Application No. 201180025543.3, 15 pages.
Chinese Office Action, dated Sep. 10, 2013, for Chinese Patent Application No. 201180025543.3, 12 pages.
Communication pursuant to Article 94(3) EPC, dated Feb. 5, 2014, for European Patent Application No. 10 720 687.2-1455, 6 pages.
Communication pursuant to Article 94(3) EPC, dated Apr. 11, 2018, for European Patent Application No. 10 720 687.2, 4 pages.
Communication pursuant to Article 94(3) EPC, dated Sep. 16, 2014, for European Patent Application No. 09 825 191.1-1464, 5 pages.
Davis et al. "Active chloride secretion in the normal human jejunum." J Clin Invest. (1980); 66(6): 1326-1333.
European Decision to Grant dated Mar. 20, 2003 in European Application No. 99964320.8.
European Decision to Grant, dated Aug. 9, 2018, for European Patent Application No. 09 825 191.1, 2 pages.
European Office Action dated Jan. 3, 2017 in European Application No. 10 720 687.2, 4 pages.
European Office Action dated Oct. 28, 2015, for European Application No. 10 720 687.2, 6 pages.
European Office Action dated Sep. 18, 2018, for European Application No. 11 760 221.9, 2 pages.
European Search Report dated Apr. 11, 2003 in European Application No. 03075658.9.
Examination Report dated Jul. 20, 2006 in Indian Application No. IN/PCT/2001/00688.
Examiner Interview Summary dated Apr. 27, 2007 in U.S. Appl. No. 10/841,709.
Examiner Interview Summary dated Aug. 16, 2012 in U.S. Appl. No. 13/446,940.
Examiner's Report dated May 4, 2004 in Australian Application No. 20590/00.
Examiner's Report dated Oct. 24, 2003 in Australian Application No. 20590/00.
Extended European Search Report dated Mar. 23, 2012 in European Patent Application No. 09825191.1.
Extended European Search Report, dated Dec. 18, 2014, for European Patent Application No. 117 60221. 9, 5 pages.
Extended European Search Report, dated Mar. 20, 2019, for European Patent Application No. 18192371.5, 8 pages.

(56) References Cited

OTHER PUBLICATIONS

Ferrara, S. D., et al., "Pharmacokinetics of Y-Hydroxybutyric Acid in Alcohol Dependent Patients After Single and Repeated Oral Doses." Br. J. Clin. Pharmacol. (1992); 34: 231-235.
Ferris, T.J., et al., "Synthesis, characterisation and detection of gamma-hydroxybutyrate salts," Forensic Science International, 2012, 216: 158-162.
Final Office Action, dated Jul. 10, 2009, for U.S. Appl. No. 11/777,877, 10 pages.
Final Office Action, dated Dec. 29, 2011, for U.S. Appl. No. 12/264,709, 23 pages.
Final Rejection dated May 13, 2013 in U.S. Appl. No. 12/773,599.
Final Office Action, dated Sep. 27, 2013, for U.S. Appl. No. 13/071,369, 10 pages.
Final Office Action, dated Dec. 23, 2014, for U.S. Appl. No. 13/071,369, 10 pages.
Final Office Action, dated Jul. 18, 2016, for U.S. Appl. No. 13/071,369, 20 pages.
Final Office Action, dated Apr. 4, 2017, for U.S. Appl. No. 13/071,369, 11 pages.
Final Office Action, dated Mar. 26, 2018, for U.S. Appl. No. 13/071,369, 12 pages.
First Office Action dated Oct. 5, 2012 in U.S. Appl. No. 12/773,599.
Final Office Action, dated Apr. 13, 2020, for U.S. Appl. No. 15/791,220, 18 pages.
Frucht, et al. "A pilot Tolerability and Efficacy Trial of Sodium Oxybate in Ethanol-Responsive Movement Disorders." Movement Disorders (2005); 20 (10): 1330-1337.
Frucht, S.J., et al., "A Single-Blind, Open-Label Trial of Sodium Oxybate for Myoclonus and Essential Tremor," Neurology (2005); 65 (12): 1967-1970.
Gallimberti, L., "Gamma-hydroxybutyric Acid for Treatment of Alcohol Withdrawal Syndrome," The Lancet, 2(8666), (1989), 787-789.
Gallimberti, L., "Gamma-Hydroxybutyric Acid in the Treatment of Alcohol Dependence: A Double-Blind Study," Alcohol Clin. Exp. Res. (1992), 16(4): 673-676.
Gerra, G., et al., "Flumazenil effects on growth hormone response to gamma-hydroxybutyric acid," Int Clin Psychopharmacol. (1994); 9 (3): 211-215.
Gessa, G. L., "Gamma-hydroxybutyric Acid in the Treatment of Alcohol Dependence," Clin. Neuropharm., vol. 15 Suppl. 1, Pt A, (1992), 303a-304a.
Gessa, G. L., et al., "Gamma-hydroxybutyric acid (GHB) for treatment of ethanol dependence," European Neuropsychopharmacology, 3(3), (1993), 224-225.
Grove-White, I. G., "Critical Flicker Frequency after Small Doses of Methohexitone, Diazepam and Sodium 4-Hydroxybutyrate." Brit. J. Anaesth (1971); 43 (2): 110-112.
Grove-White, I. G., et al., "Effect of Methohexitone, Diazepam and Sodium 4-Hydroxybutyrate on Short-Term Memory." Brit. J. Anaesth (1971); 43 (2): 113-116.
Hasenbos, M.A., et al., "Anaesthesia for bullectomy. A technique with spontaneous ventilation and extradural blockade." Anaesthesia (1985); 40 (10): 977-980.
Hoes, M. J., "Gamma-hydroxybutyric acid () as hypnotic. Clinical and pharmacokinetic evaluation of gammahydroxybutyric acid as hypnotic in man," L'Encephale: Revue de psychiatrie clinique biologique et thérapeutique (1980); 6 (1): 93-99.
Indian Examination Report dated Jun. 27, 2018 for Indian Patent Application No. 8310/DELNP/2012, 5 pages.
International Preliminary Examination Report dated Mar. 26, 2001 in International Application No. PCT/US99/30740.
International Search Report dated Jul. 21, 2000 in International Application No. PCT/US99/30740.
Israeli Office Action dated Nov. 14, 2016 for Israeli Patent Application No. 222161, 2 pages.
Israeli Office Action dated Nov. 9, 2016 for Israeli Patent Application No. 222012, 2 pages.
Israeli Office Action, dated Jul. 6, 2015, for Israeli Patent Application No. 222161, 3 pages.
Israeli Office Action, dated Jun. 17, 2015, for Israeli Patent Application No. 222012, 2 pages.
Japanese Office Action, dated Dec. 17, 2013, for Japanese Patent Application No. 2011-534614, 3 pages.
Japanese Office Action, dated Jun. 16, 2015, for Japanese Patent Application No. 2013-509036, 1 page.
Japanese Office Action, dated Jun. 24, 2014, for Japanese Patent Application No. 2011-534614, 2 pages.
Japanese Office Action, dated Jun. 3, 2014, for Japanese Patent Application No. 2013-509036, 6 pages.
Japanese Office Action, dated May 12, 2015, for Japanese Patent Application No. 2011-534614, 2 pages.
Japanese Notice to Grant, dated Sep. 1, 2015, for Japanese Patent Application No. 2011-534614, 2 pages.
Japanese Notice to Grant, dated Mar. 29, 2016, for Japanese Patent Application No. 2013-509036, 4 pages (with English Translation).
Japanese Notice to Grant, dated Jun. 7, 2016, for Japanese Patent Application No. 2013-501486, 6 pages (with English Translation).
Japanese Office Action, dated Nov. 10, 2015, for Japanese Patent Application No. 2013-501486, 3 pages.
Japanese Office Action, for Japanese Patent Application No. 2013-501486, dated Mar. 3, 2015, 7 pages. (with English Translation).
*Jazz Pharmaceuticals, Inc.* v *Roxane Laboratories, Inc.*, Civil Action No. 12-6761 (ES)(SCM) Identity of Prior Art Pursuant to Local Patent Rule 3.3(a), (2013).
Laborit, H., "Gamma-Hydroxybutyrate, Succinic Semialdehyde and Sleep," Laboratoire d'Eutonologie, (1973), 257-274.
Ladinsky, et al., "Mediation by the Corticostriatal Input of the In Vivo increase in Rat Striatal Acetylcholine content induced by 2-Chloroadenosine," Biochemical Pharm. (1983); 32 (19): 2993-2996.
Ladinsky, H., et al., "Mode of Action of Gamma-Butyrolactone on the Central Cholinergic System, Naunyn-Schmiedeberg's," Arch. Pharmacol. (1983); 322 (1): 42-48.
Lammers, G. J., "Gammahydroxybutyrate and Narcolepsy: A Double-Blind Placebo-Controlled Study." Sleep (1993); 16 (3): 216-220.
Lapierre et al., "The Effect of Gamma-Hydroxybutyrate: A Double-Blind Study of Normal Subjects," Sleep Research (1988); 17:99, 1988, 6 pages. (Abstract Only).
Lapierre, O., "The Effect of Gamma-Hydroxybutyrate on Nocturnal and Diurnal Sleep of Normal Subjects: Further Considerations on REM Sleep-Triggering Mechanisms." Sleep (1990); 13 (1): 24-30.
Lee C. R.,"Evidence for the β-oxidation of orally administered 4-hydroxybutyrate in humans." Biochemical Medicine (1977); 17 (3): 284-291.
Lettieri and Fung, "Improved pharmacological activity via pro-drug modification: comparative pharmacokinetics of sodium gamma-hydroxybutyrate and gamma-butyrolactone." Research Communications in Chemical Pathology and Pharmacology (1978); 22 (1): 107-118.
Lubrano, et al. "Fibromyalgia in Patients with Irritable Bowel Syndrome. An Association with the Severity of the Intestinal Disorder." Int J Colorectal Dis. (2001); 16 (4): 211-215.
Mahore et al. "Ion exchange resins: pharmaceutical applications and recent advancement." Int J Pharm Sci Rev Res (2010); 1.2: 8-13.
Mamelak, et al. The Effects of γ-Hydroxybutyrate on Sleep. Biol Psych (1977); 12 (2): 273-288.
Mamelak, M., "Gammahydroxybutyrate: An endogenous regulator of energy metabolism." Neuroscience and Biobehavioral Reviews (1989); 13 (4): 187-198.
Mamelak, M., "Sleep-Inducing Effects of Gammahydroxybutyrate." The Lancet (1973); 302 (7824): 328-329.
Mamelak, M., et al., "Treatment of Narcolepsy and Sleep Apnea with Gammahydroxybutyrate: A clinical and polysomnographic case study." Sleep (1981); 4 (1): 105-111.
Mamelak, M., et al., "Treatment of Narcolepsy with y-hydroxybutyrate. A review of Clinical and Sleep Laboratory Findings." Sleep (1986); 9 (1): 285-290.

(56) References Cited

OTHER PUBLICATIONS

Markman Opinion, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES.
Mexican Office Action dated Jan. 9, 2018, for Mexican Patent Application No. MX/a/2012/011022, 3 pages.
Mexican Office Action, dated Apr. 4, 2014, for Mexican Patent Application No. MX/a/2012/012729, 3 pages.
Mexican Office Action, dated Dec. 30, 2014, for Mexican Patent Application No. MX/a/2012/012729, 3 pages.
Mexican Office Action, dated Jul. 3, 2015, for Mexican Patent Application No. MX/a/2012/012729, 3 pages.
Mexican Office Action, dated Sep. 10, 2013, for Mexican Patent Application No. MX/a/2012/012729, 3 pages.
Moldofsky et al. "A Chronobiologic Theory of Fibromyalgia." J. Muscoloskel. Pain, 1, 49 (1993).
Moldofsky, et al. "Musculoskeletal Symptoms and Non-REM Sleep Disturbance in Patients with 'Fibrositis Syndrome' and Healthy Subjects." Psychosom. Med. (1975); 37 (4): 341-351.
Morrison, Robert Thornton, et al., Organic Chemistry, 3rd Edition, (1973), pp. 672-677.
Nema, S, et al., "Excipients and Their Use in Injectable Products." PDA J. Pharm. Sci. Technol. (1997); 51(4): 166-171.
Neuman, Ariel, "GHB's Path to Legitimacy: An Administrative and Legislative History of Xyrem." Apr. 2004, Harvard Law School, Class of 2005, Food and Drug Law, Winter Term 2004, Professor Peter Barton Hutt. (2004), 1-39.
Non-Final Office Action, dated Feb. 27, 2013, for U.S. Appl. No. 13/071,369, 8 pages.
Non-Final Office Action, dated Jun. 20, 2014, for U.S. Appl. No. 13/071,369, 12 pages.
Non-Final Office Action, dated Oct. 22, 2015, for U.S. Appl. No. 13/071,369, 17 pages.
Non-Final Office Action, dated Jul. 1, 2015, for U.S. Appl. No. 14/295,098, 18 pages.
Non-Final Office Action, dated Jun. 26, 2018, for U.S. Appl. No. 15/047,586, 15 pages.
Non-Final Office Action, dated Aug. 2, 2019, for U.S. Appl. No. 15/791,220, 12 pages.
Notice of Allowance dated Jan. 30, 2013 in U.S. Appl. No. 13/182,324.
Notice of Allowance dated Feb. 5, 2013 in Japanese Application No. 2009-028694.
Notice of Allowance dated Mar. 24, 2004 in U.S. Appl. No. 10/194,021.
Notice of Allowance dated Apr. 18, 2002 in U.S. Appl. No. 09/470,570.
Notice of Allowance dated Jun. 16, 2009 in Japanese Application No. 2000-590626.
Notice of Allowance dated Jul. 2, 2006 in Israeli Application No. 143733.
Notice of Allowance dated Jul. 16, 2012 in U.S. Appl. No. 13/446,940.
Notice of Allowance dated Oct. 3, 2012 in U.S. Appl. No. 13/446,892.
Notice of Allowance dated Oct. 8, 2010 in U.S. Appl. No. 11/777,877.
Notice of Allowance dated Dec. 3, 2004 in Canadian Application No. 2,355,293.
Notice of Allowance dated May 25, 2007 in U.S. Appl. No. 10/841,709.
Notice of Allowance, dated Mar. 27, 2014, for U.S. Appl. No. 12/264,709, 9 pages.
Notice of Allowance, dated Mar. 27, 2014, for U.S. Appl. No. 12/773,599, 9 pages.
Notice of Allowance, dated Mar. 6, 2014, for U.S. Appl. No. 13/787,437, 8 pages.
Notice of Allowance, dated Nov. 25, 2013, for U.S. Appl. No. 13/787,437, 9 pages.
Notice of Allowance, dated Sep. 26, 2017, for U.S. Appl. No. 14/295,098, 8 pages.
Notification Concerning Transmittal of International Preliminary Report on Patentability dated May 19, 2011 in International Application No. PCT/US2009/061312, now W02010/053691.
Notification Concerning Transmittal of International Preliminary Report on Patentability dated Nov. 15, 2012 in International Application No. PCT/US2010/033572.
Notification Concerning Transmittal of the International Preliminary Report on Patentability dated Oct. 4, 2012 in International Application No. PCT/US2011/029802.
Notification of the International Search Report and the Written Opinion of the International Searching Authority dated Jan. 18, 2011 in International Application No. PCT/US2010/033572.
Notification of the International Search Report and the Written Opinion of the International Searching Authority dated Dec. 18, 2009 in International Application No. PCT/US2009/061312.
Notification of Transmittal of the International Search Report and the Written Opinion of the International Searching Authority dated May 17, 2011 in International Application No. PCT/US2011/029802, now W02011/119839.
Office Action dated Nov. 29, 2016 in U.S. Appl. No. 14/295,098, 10 pages.
Office Action dated Dec. 6, 2013 in U.S. Appl. No. 12/264,709, 33 pages.
Office Action dated May 25, 2012 in U.S. Appl. No. 12/913,644.
Office Action dated May 25, 2001 in U.S. Appl. No. 09/470,570.
Office Action dated Jun. 11, 2012 in U.S. Appl. No. 13/446,940.
Office Action dated Jun. 28, 2012 in U.S. Appl. No. 13/446,892.
Office Action dated Jun. 30, 2004 in Canadian Application No. 2,355,293.
Office Action dated Jul. 6, 2011 in U.S. Appl. No. 12/264,709, now US 2010/0112056.
Office action dated Jul. 16, 2012 in U.S. Appl. No. 13/182,324.
Office Action dated Jul. 31, 2012 in Japanese Application No. 2009-028694.
Office Action dated Jan. 17, 2012 Japanese Application No. 2009-028694.
Office Action dated Oct. 5, 2006 in Japanese Application No. 2000-590626.
Office Action dated Oct. 25, 2001 in U.S. Appl. No. 09/470,570.
Office Action dated Nov. 6, 2008 in U.S. Appl. No. 11/777,877.
Office Action dated Nov. 19, 2012 in Indian Application No. 2633/KOLNP/2007.
Office Action dated Nov. 21, 2001 in European Application No. 99964320.8.
Office Action dated Nov. 30, 2006 in U.S. Appl. No. 10/841,709.
Office Action dated Dec. 6, 2013 in U.S. Appl. No. 12/264,709.
Office Action dated Dec. 13, 2001 in U.S. Appl. No. 09/470,570.
Office Action dated Feb. 3, 2010 in U.S. Appl. No. 11/777,877.
Office Action, dated Aug. 24, 2012, for U.S. Appl. No. 13/446,892, 13 pages.
Office Action, dated Feb. 27, 2002, for European Application No. 99964320.8, 10 pages.
Office Action, dated Oct. 10, 2013, for U.S. Appl. No. 13/787,437, 8 pages.
Office Action, dated Oct. 5, 2012, for U.S. Appl. No. 12/773,599, 8 pages.
Ohta et al. "Development of a simple method for the preparation of a silica gel based controlled delivery system with a high drug content." European Journal of Pharmaceutical Sciences (2005); 26.1: 87-96.
Ondo, William G., et al., "Sodium Oxybate for Excessive Daytime Sleepiness in Parkinson's Disease: A Polysomnographic Study." Arch. Neural. (2008); 65 (10): 1337-1340.
Order, filed Sep. 14, 2012, in the case of *Jazz Pharmaceuticals, Inc.*, Plaintiff, v. *Roxane Laboratories, Inc.*, Defendant (United States District Court for the District of New Jersey, Civil 10-6108 ES), (Sep. 14, 2012).
Outlaw, et al. "Dyspepsia and its Overlap with Irritable Bowel Syndrome." Curr Gastroenterol Rep. (2006); 8 (4): 266-272.
Palatini, P., "Dose Dependent Absorption and Elimination of Gamma-Hydroxybutyric Acid in Healthy Volunteers." Eur. J. Clin. Pharmacol. (1993); 45 (4): 353-356.

(56) References Cited

OTHER PUBLICATIONS

Patent Withdrawal Notice, withdrawn Jun. 18, 2014, for U.S. Appl. No. 13/787,437, 1 page.
Patil et al. "A review on ionotropic gelation method: novel approach for controlled gastroretentive gelispheres." International Journal of Pharmacy and Pharmaceutical Sciences (2012); 4.4: 27-32.
Petition to Withdraw from Issue Under 37 C.F.R. 1.313(c)(1) or (2), dated Jun. 17, 2014, for U.S. Appl. No. 13/787,437, 1 page.
Preliminary Amendment filed Jan. 10, 2011 in U.S. Appl. No. 12/913,644.
Preliminary Amendment filed Feb. 19, 2013 in U.S. Appl. No. 13/685,561.
Preliminary Amendment filed Jul. 11, 2002 in U.S. Appl. No. 10/194,021.
Preliminary Amendment filed Nov. 29, 2001 in U.S. Appl. No. 09/470,570.
Preliminary Amendment filed May 8, 2004 in U.S. Appl. No. 10/841,709.
Preliminary Amendment, filed Mar. 7, 2013, for U.S. Appl. No. 13/787,437, 31 pages.
Prosecution for U.S. Appl. No. 13/787,437, 33 pages.
Puguan et al. "Diffusion characteristics of different molecular weight solutes in Ca—alginate gel beads." Colloids and Surfaces A: Physicochemical and Engineering Aspects (2015); 469: 158-165.
Remington. The Science and Practice of Pharmacy. 20th Edition, Gennaro, Ed,. Lippincott Williams &Wilkins (2000). (See e.g. p. 861).
Remington. The Science and Practice of Pharmacy. 20th Edition, Gennaro, Ed,. Lippincott Williams & Wilkins. Chapter 45 (Oral Solid Dosage Forms) (2000).
Response filed Jan. 11, 2010 to Final Office Action dated Jul. 10, 2009 in U.S. Appl. No. 11/777,877.
Response filed Jan. 13, 2009 to Final Office Action dated Oct. 14, 2008 in Japanese Application No. 2000-590626.
Response filed Jan. 16, 2013 to Office Action dated Jul. 16, 2012 in U.S. Appl. No. 13/182,324.
Response filed Jan. 17, 2013 to Office Action dated Jul. 31, 2012 in Japanese Application No. 2009-028694.
Response filed Feb. 16, 2001 to Written Opinion dated Oct. 18, 2000 in International Application No. PCT/US99/30740.
Response filed Feb. 27, 2002 to Office Action dated Nov. 21, 2001 in European Application No. 99964320.8.
Response filed Apr. 10, 2007 to Office Action dated Oct. 10, 2006 in Japanese Application No. 2000-590626.
Response filed Jun. 19, 2012 to Office Action dated Jan. 17, 2012 in Japanese Application No. 2009-028694.
Response filed Jul. 2, 2012 to Office Action issued Jun. 11, 2012 in U.S. Appl. No. 13/446,940.
Response filed Jul. 9, 2007 to Examination Report dated Jul. 20, 2006 in Indian Application No. IN/PCT/2001/00688.
Response filed Jul. 31, 2008 to Restriction Requirement dated Jul. 14, 2008 in U.S. Appl. No. 11/777,877.
Response filed Aug. 24, 2012 to Office Action dated Jun. 28, 2012 in U.S. Appl. No. 13/446,892.
Response filed Oct. 19, 2004 to Office Action dated Jun. 30, 2004 in Canadian Application No. 2,355,293.
Response filed Nov. 19, 2004 to Examiner's Report dated May 4, 2004 in Australian Application No. 20590/00.
Response filed Feb. 21, 2007 to Office Action dated Nov. 30, 2006 in U.S. Appl. No. 10/841,709.
Response filed Apr. 2, 2009 to Office Action dated Nov. 6, 2008 in U.S. Appl. No. 11/777,877.
Response filed Jul. 28, 2010 to Office Action dated Feb. 3, 2010 in U.S. Appl. No. 11/777,877.
Response to Jul. 6, 2011 Office Action filed on Oct. 6, 2011 in U.S. Appl. No. 12/264,709, now US 2010/0112056.
Response to Dec. 29, 2011 Final Office Action filed Feb. 29, 2012 in U.S. Appl. No. 12/264,709, now us 2010/0112056.
Response to Final Office Action filed Nov. 13, 2013 in U.S. Appl. No. 12/773,599.
Response to First Office Action filed Jan. 4, 2013 in U.S. Appl. No. 12/773,599.
Response to Office Action filed Mar. 6, 2002 in U.S. Appl. No. 09/470,570.
Response to Office Action filed Aug. 10, 2001 in U.S. Appl. No. 09/470,570.
Response to Office Action, dated Feb. 3, 2010, for U.S. Appl. No. 11/777,877, 11 pages.
Response to Office Action, dated Nov. 6, 2008, for U.S. Appl. No. 11/777,877, 11 pages.
Response to Restriction Requirement filed May 3, 2001 in U.S. Appl. No. 09/470,570.
Response to Rule 312 Communication, dated May 13, 2014, for U.S. Appl. No. 13/787,437.
Response to the Mar. 12, 2012 Advisory Action filed Jun. 29, 2012 in U.S. Appl. No. 12/264,709, now us 2010/0112056.
Restriction Requirement issued Mar. 19, 2001 in U.S. Appl. No. 09/470,570.
Restriction Requirement dated Jul. 14, 2008 in U.S. Appl. No. 11/777,877.
Restriction Requirement, dated Mar. 3, 2015, for U.S. Appl. No. 14/295,098, 9 pages.
Roth, et al., "γ-Butyrolactone and γ-Hydroxybutyric Acid-I, Distribution and Metabolism." Biochemical Pharmacology (1966); 15 (9):1333-1348.
Roth, R. H., et al., "γ-Butyrolactone and γ-Hydroxybutyric acid-II. The Pharmacologically active form." J. Neuropharmacol. (1966); 5 (6): 421-428.
Roxane Laboratories, Inc.'s Answer and Affirmative Defenses to Plaintiff's Complaint, (Jan. 4, 2013).
Roxane Laboratories, Inc.'s Answer, Affirmative Defenses and Counterclaims to Plaintiff's Complaint, (Dec. 29, 2010).
Roxane Laboratories, Inc.'s Answer, Affirmative Defenses and Counterclaims to Plaintiff's Complaint, (Jun. 1, 2011).
Roxane Laboratories, Inc.'s Answer, Affirmative Defenses and Counterclaims to Plaintiff's Complaint, (Mar. 9, 2011).
Roxane Laboratories, Inc.'s Answer, Affirmative Defenses and Counterclaims to Plaintiff's Complaint, (Nov. 9, 2012).
Roxane Laboratories, Inc.'s Intitial Invalidity and Noninfringement Contentions Pursuant to Local Patent Rule 3.6, (Apr. 14, 2011).
Russell, I. Jon, et al., "Sodium Oxybate Relieves Pain and Improves Function in Fibromyalgia Syndrome." Arthritis. Rheum. (2009); 60 (1): 299-309.
Scharf, et al., "Effect of Gamma-Hydroxybutyrate on Pain, Fatigue, and the Alpha Sleep Anomaly in Patients with Fibromyalgia," (1998) J. Rheumatol. (1998) 25:1986-1990.
Scharf, M. B., "The Effects and Effectiveness of γ-Hydroxybutyrate in Patients with Narcolepsy." J. Clin. Psychiatry (1985); 46 (6): 222-225.
Scharf, M. B., et al., "GHB—New Hope for Narcoleptics?" Biol Psychiatry (1989); 26 (4): 329-330.
Scharf, Martin B. et al., "The Effects of Sodium Oxybate on Clinical Symptoms and Sleep Patterns in Patients with Fibromyalgia." J. Rheumatol. (2003); 30 (5): 1070-1074.
Scrima, et al., "Effect of Gamma-Hydroxybutyrate on a Patient with Obstructive Sleep Apnea." Sleep Research (1987); 16: 137.
Scrima, et al., "Effect of High Altitude on a Patient with Obstructive Sleep Apnea." Sleep Research (1987); 16: 427.
Scrima, et al., "Effects of Gamma-Hydroxybutyrate (GHB) on Narcolepsy-Cataplexy Symptoms and MSLT Results in Male and Female Patients." Association of Professional Sleep Societies (1988); 251.
Scrima, et al., "Gamma-Hydroxybutyrate Effects on Cataplexy and Sleep Attacks in Narcoleptics." Sleep Research (1987); 16: 134.
Scrima, L., "The Effects of γ-Hydroxybutyrate on the Sleep of Narcolepsy Patients: A Double-Blind Study." Sleep (1990); 13 (6): 479-490.
Scrima, L., et al., "Efficacy of Gamma-Hydroxybutyrate Versus Placebo in Treating Narcolepsy-Cataplexy: Double-Blind Subjective Measures," Biol. Psychiatry (1989); 26 (4): 331-343.
Scrima, L., et al., "Narcolepsy." New England J. Med. (1991); 324 (4): 270-272.

(56) References Cited

OTHER PUBLICATIONS

Search Report dated Jan. 22, 2004 in Australian Application No. 20590/00.
Seno and Yamabe. "The Rheological Behavior of Suspensions of Ion-exchange Resin Particles." Bulletin of the Chemical Society of Japan (1966); 39.4: 776-778.
Series, F., "Effects of Enhancing Slow-Wave Sleep by Gamma-Hydroxybutyrate on Obstructive Sleep Apnea." Am. Rev. Respir. Dis. (1992); 145 (6): 1378-1383.
Singh et al. "Ion exchange resins: drug delivery and therapeutic applications." Fabad J. Pharm. Sci (2007); 32: 91-100.
Snead, et al., "Ontogeny of y-Hydroxybutyric Acid. I. Regional Concentration in Developing Rat, Monkey and Human Brain." Brain Res. (1981); 227 (4): 579-589.
Snead, O. Carter, "γ-Hydroxybutyrate Model of Generalized Absence Seizures: Further Characterization and Comparison with Other Absence Models." Epilepsia (1988); 29 (4): 361-368.
Srikanth et al., "Ion-exchange resins as controlled drug delivery carriers." Journal of Scientific Research (2010); 2.3: 597-611.
Stock, G., "Increase in brain dopamine after axotomy or treatment with Gammahydroxybutyric acid due to elimination of the nerve impulse flow." Naunyn-Schmiedeberg's Arch. Pharmacol. (1973); 278 (4): 347-361.
Strong, A.J., "γ-Hydroxybutyric acid and intracranial pressure." The Lancet (1984); 1 (8389): 1304.
Suner, Selim, et al., "Pediatric Gamma Hydroxybutyrate Intoxication." Acad Emerg. Med. (1997); 4 (11): 1041-1045.
Supplemental Preliminary Amendment filed Mar. 5, 2013 in U.S. Appl. No. 13/685,561.
Supplemental Preliminary Amendment filed Apr. 13, 2012 in U.S. Appl. No. 13/182,324.
Supplementary Notice of Allowance dated Sep. 17, 2002 in U.S. Appl. No. 09/470,570.
Takka and Gürel. "Evaluation of chitosan/alginate beads using experimental design: formulation and in vitro characterization." AAPS PharmSciTech (2010); 11.1: 460-466.
The Dow Chemical Company, Product Data Sheet for AMBERLITE™ IRN78 Resin. Form No. 177-02230-0311, Rev. 0, 3 pages.
Transcript of a Markman Hearing, dated Apr. 26, 2012, in the case of *Jazz Pharmaceuticals, Inc.*, Plaintiff, v. *Roxane Laboratories, Inc.*, Defendant (United States District Court for the District of New Jersey, Civil 106108 ES), (Apr. 26, 2012).
Tunnicliff, Godfrey, "Sites of Action of Gamma-Hydroxybutyrate (GHB)—A Neuroactive Drug with Abuse Potential." Clinical Toxicology (1997); 35 (6): 581-590.
Turnberg, L.A. "Abnormalities in intestinal electrolyte transport in congenital chloridorrhoea." Gut. (1971); 12(7): 544-551.
United States Pharmacopeial Convention, Inc.: The National Formulary, 23/NF18, (1995), p. 2205.

Unknown author, title: definition of biotransformation; Medical dictionary; downloaded Jun. 21, 2018 (Year: 2018).
Van Den Bogert, A. G., et al., "Placentatransfer of 4-hydroxybutyric acid in man," Anaesthesiology and Intensive Care Medicine (1978); 110: 55-64.
Vickers, M.D., "Gammahydroxybutyric Acid." Int. Anesth. Clinic (1969); 7 (1): 75-89.
Wermuth (Ed.), The Practice of Medicinal Chemistry, Academic Press, Third Edition, "Preparation of Water-Soluble Compounds Through Salt Formulation," Chapter 37, 2008, p. 758, 6 pages.
World Health Organization, "Annex 7: Multisource (generic) pharmaceutical products: guidelines on registration requirements to establish interchangeability," WHO Expert Committee on Specifications for Pharmaceutical Preparations Fortieth Report, pp. 347-390, 2006, retrieved from http://apps.who.int/prequal/info_general/documents/TRS937/WHO_TRS_937_eng.pdf#page=359.
Written Opinion dated Oct. 18, 2000 in International Application No. PCT/US99/30740.
Yamada, Y., "Effect of Butyrolactone and Gamma-Hydroxybutyrate on the EEG and Sleep Cycle in Man," Electroencephalography and Clinical Neurophysiology (1967); 22 (6): 558-562.
Zheng (Ed.), "Formulation and Analytical Development for Low-Dose Oral Drug Products," John Wiley & Sons, Inc., Hoboken, New Jersey, Table 4.1, p. 65, 2009, 3 pages.
Baldrick, P., "Pharmaceutical Excipient Development: The Need for Preclinical Guidance," Regul. Toxicol. Pharmacol. Oct. 2000 32(2):210-218.
Bodmeier, R., "Tableting of coated pellets," European Journal of Pharmaceutics and Biopharmaceutics, (1997) 43(1), 1-8.
Gallimberti et al., "Clinical efficacy of gamma-hydroxybutyric acid in treatment of opiate withdrawal," Eur Arch Psychiatry Clin Neurosci. 1994;244(3):113-114.
Gallimberti et al., "Gamma-Hydroxybutyric Acid for Treatment of Opiate Withdrawal Syndrome," Neuropsychopharmacology, 1993, vol. 9, No. 1, pp. 77-81.
International Search Report and Written Opinion of the International Searching Authority for International Application No. PCT/US2019/062237.
Rubbens et al., "Gastric and Duodenal Ethanol Concentrations after intake of Alcoholic Beverages in Postprandial Conditions," Molecular Pharmaceutics, (2017) 14(12):4202-4208.
Shah et al., "In vitro Dissolution Profile Comparison—Statistics and Analysis of the Similarity Factor, f2," Pharm Research, (1998) 15(6):889-896.
U.S. Department of Health and Human Services et al., "Dissolution Testing of Immediate Release Solid Oral Dosage Forms," Food and Drug Administration, CDER, Aug. 1997, 17 pages.
U.S. Department of Health and Human Services et al., "Extended Release Oral Dosage Forms: Development, Evaluation, and Application of In Vitro/In Vivo Correlations", Food and Drug Administration, CDER, Sep. 1997, 27 pages.
Walden et al., "The Effect of Ethanol on the Release of Opioids 30 from Oral Sustained-Release Preparations," Drug Development and Industrial Pharmacy, 2007, 33:10, 1101-1111.

CONTROLLED RELEASE DOSAGE FORMS FOR HIGH DOSE, WATER SOLUBLE AND HYGROSCOPIC DRUG SUBSTANCES

RELATED APPLICATIONS

This application is a continuation of U.S. patent application Ser. No. 16/712,260, filed Dec. 12, 2019, which is a continuation of U.S. patent application Ser. No. 16/025,487, filed Jul. 2, 2018, which is a continuation of U.S. patent application Ser. No. 13/071,369, filed Mar. 24, 2011, now abandoned, which claims the benefit of U.S. Provisional Application No. 61/317,212, filed on Mar. 24, 2010, the contents of each of which are incorporated herein by reference.

TECHNICAL FIELD

This disclosure relates to controlled release drug compositions.

BACKGROUND

For some drugs, it is difficult to formulate a controlled release dosage form that maintains an effective concentration of the drug over a sustained period of time. In particular, drugs that are administered at a high dose, drugs having a low molecular weight, and drugs with high water solubility make formulation of a controlled release dosage form challenging. For example, in the context of a controlled release drug formulation produced as a unit dosage form for oral administration, drugs that must be administered at a high dose constrain the amount of rate controlling excipients that can be used in formulating a drug composition that is both capable of sustained delivery of therapeutic doses of the drug and exhibits a size and shape suited to oral administration. Low molecular weight and high-solubility drugs may also readily permeate films and matrices that might otherwise be used to control release, and high solubility drugs are not suited to some drug delivery approaches, particularly where zero-order release kinetics are desired. An example of a drug that is administered at a high dose, has a low molecular weight, and high water solubility, is gamma-hydroxy butyrate (GHB), particularly the sodium salt of GHB Initial interest in the use of GHB as a potential treatment for narcolepsy arose from observations made during the use of GHB for anesthesia. Unlike traditional hypnotics, GHB induces sleep that closely resembles normal, physiologic sleep (Mamelak et al., Biol Psych 1977:12:273-288). Therefore, early investigators administered GHB to patients suffering from disorders of disturbed sleep, including narcolepsy (Broughton et al. in Narcolepsy, NY, N.Y.: Spectrum Publications, Inc. 1976:659-668), where it was found to increase total nocturnal sleep time, decrease nocturnal awakenings and increase Stage 3-4 (slow wave) sleep. Three open-label and two placebo-controlled studies provided a body of evidence demonstrating that improvements in nocturnal sleep were associated with a reduction in cataplexy and improvements in excessive daytime sleepiness (Broughton et al., Can J. Neurol Sci 1979; 6:1-6, and Broughton et al., Can J. Neurol Sci 1980; 7:23-30).

An estimated 6 million Americans suffer the often baffling symptoms of fibromyalgia or chronic fatigue syndrome. Patients with fibromyalgia, also referred to as fibromyalgia syndrome, FMS or fibrositis syndrome, report widespread musculoskeletal pain, chronic fatigue, and non-restorative sleep. These patients show specific regions of localized tenderness in the absence of demonstrable anatomic or biochemical pathology, and patients suffering from fibromyalgia typically describe light and/or restless sleep, often reporting that they awaken feeling unrefreshed with pain, stiffness, physical exhaustion, and lethargy. See, H. D. Moldofsky et al., J. Muscoloskel. Pain, 1, 49 (1993). In a series of studies, Moldofsky's group has shown that aspects of the patients' sleep pathology are related to their pain and mood symptoms. That is, patients with fibrositis syndrome show an alpha (7.5 to 11 Hz) electroencephalographic (EEG), non-rapid-eye-movement (NREM) sleep anomaly correlated with musculoskeletal pain and altered mood. Moldofsky has interpreted this alpha EEG NREM sleep anomaly to be an indicator of an arousal disorder within sleep associated with the subjective experience of non-restorative sleep. See H. D. Moldofsky et al., Psychosom. Med., 37, 341 (1975).

Fibromyalgia patients frequently report symptoms similar to those of patients with post-infectious neuromyasthenia, also referred to as chronic fatigue syndrome (CFS). CFS is a debilitating disorder characterized by profound tiredness or fatigue. Patients with CFS may become exhausted with only light physical exertion. They often must function at a level of activity substantially lower than their capacity before the onset of illness. In addition to these key defining characteristics, patients generally report various nonspecific symptoms, including weakness, muscle aches and pains, excessive sleep, malaise, fever, sore throat, tender lymph nodes, impaired memory and/or mental concentration, insomnia, and depression. CFS can persist for years. Compared with fibromyalgia patients, chronic fatigue patients have similarly disordered sleep, localized tenderness, and complaints of diffuse pain and fatigue.

Scharf et al. conducted an open-label study to evaluate the effects of GHB on the sleep patterns and symptoms of non-narcoleptic patients with fibromyalgia (Scharf et al., J Rheumatol 1998; 25: 1986-1990). Eleven patients with previously confirmed diagnosis of fibromyalgia who reported at least a 3-month history of widespread musculoskeletal pain in all body quadrants and tenderness in a least 5 specific trigger point sites participated in the study. Results showed that patients reported significant improvements in the subjective assessments of their levels of pain and fatigue over all 4 weeks of GHB treatment as compared to baseline, as well as a significant improvement in their estimates of overall wellness before and after GHB treatment.

WO 2006/053186 to Frucht describes an open label study of 5 patients with hyperkinetic movement disorders including ethanol responsive myoclonus and essential tremor. Sodium oxybate, a sodium salt of GHB, was reported to produce dose-dependent improvements in blinded ratings of ethanol responsive myoclonus and tremor and was said to be tolerated at doses that provided clinical benefit.

XYREM® sodium oxybate oral solution, the FDA approved treatment for cataplexy and excessive daytime sleepiness associated with narcolepsy, contains 500 mg sodium oxybate/ml water, adjusted to pH=7.5 with malic acid. In man, the plasma half-life of sodium oxybate given orally is about 45 minutes and doses of 2.25 grams to 4.5 grams induce about 2 to 3 hours of sleep (See, L. Borgen et al., J. Clin. Pharmacol., 40, 1053 (2000)). Due to the high doses required and very short half-life of sodium oxybate, optimal clinical effectiveness in narcolepsy typically requires dosing of the drug twice during the night, with administration typically recommended at 2.5 to 4 hour intervals. For each dose, a measured amount of the oral solution is removed from the primary container and transferred to a separate container where it is diluted with water before administration. The second dose is prepared at bedtime and stored for administration during the night.

Liang et al. (published U.S. patent application US 2006/0210630 A1) disclose administration of GHB using an immediate release component and a delayed release component. The delayed release component of the formulations taught in Liang et al., however, function in a pH dependent manner.

DETAILED DESCRIPTION

Figure 1:
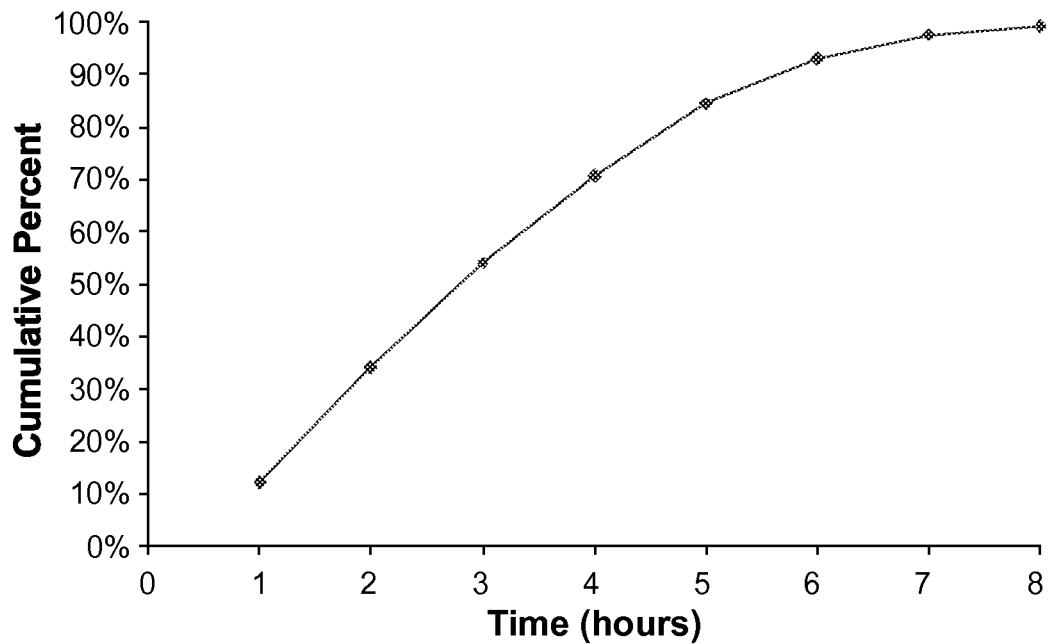
FIG. 1 shows the delivery profile of sodium oxybate controlled release formulations as described herein.

Formulations and dosage forms for the controlled release of a drug are described herein. Formulations described herein are suited to the controlled release of high dose drugs that are highly water soluble. In addition, in certain embodiments, the formulations described herein provide controlled release of drugs that are highly hygroscopic, even where such drugs must be administered at relatively high doses. In particular embodiments, the controlled release formulations are provided as a unit dosage form, and in one such embodiment, the controlled release formulation is provided as a coated tablet.

The formulations and dosage forms of the present invention can also include an immediate release component. The immediate release component can form part of a controlled release (CR) unit dosage form or may be a separate immediate release composition. Therefore, an immediate release (IR) component may be provided, for example, as a dry powder formulation, an immediate release tablet, an encapsulated formulation, or a liquid solution or suspension. However, the IR component may also be formulated as part of a single dosage form that integrates both the IR and CR components. In such an embodiment, the pharmaceutical formulation may be provided in the form of the coated tablet or capsule.

In specific embodiments, controlled release and immediate release formulations can be dosed together to a subject to provide quick onset of action, followed by maintenance of therapeutic levels of the drug substance over a sustained period of time. However, because the controlled release component and immediate release component described herein need not be present in a single dosage form, as it is used herein, the phrase "dosed together" refers to substantially simultaneous dosing of the controlled release and immediate release components, but not necessarily administration in the same dosage form. Dosing the controlled release and immediate release components together offers increased convenience, allowing patients to quickly achieve and maintain therapeutic levels of a drug over a sustained period of time, while reducing the frequency with which the drug must be dosed. Furthermore, dosing the controlled release and immediate release components together may avoid the disadvantages of dosing regimens and formulations that result in highly pulsatile plasma concentrations.

An example of a drug that may be used with the controlled release dosage forms described herein is GHB. It should be noted that embodiments of controlled release dosage forms comprising GHB, and other drugs, are presented herein for purposes of example only and not for purposes of limitation. The formulations and unit dosage forms provided herein can be utilized to achieve controlled release of GHB, as well as pharmaceutically acceptable salts, hydrates, tautomers, solvates and complexes of GHB. Suitable salts of GHB include the calcium, lithium, potassium, sodium and magnesium salts. The structure of the sodium salt of GHB, sodium oxybate, is given as formula (I):

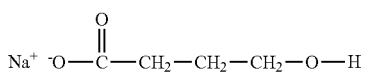

Methods of making GHB salts are described, for example, in U.S. Pat. No. 4,393,236, which is incorporated herein by reference.

Formulating GHB into a unit dosage form presents various challenges, and such challenges are magnified in the context of formulating a unit dosage form providing controlled release of GHB. For instance, GHB is very soluble, generally requires a relatively high dose, has a low molecular weight, and exhibits a short circulating half-life once administered. Therefore, a controlled release unit dosage form of GHB should be configured to deliver large doses of drug over a prolonged period of time, while being acceptably sized for oral administration. However, controlled release formulations typically require the addition of significant amounts of excipients or rate controlling materials to control the delivery of drug, and the presence and need for such materials often limits the drug loading available for a given controlled release technology. Additionally, low molecular weight drugs, such as GHB, typically exhibit high permeability through films and matrices. Even further, high water solubility increases drug mobility and may preclude the use of some approaches utilized to achieved a controlled release dosage form.

Another challenge to achieving a formulation capable of delivering GHB over a sustained period of time is the fact that some forms of GHB, such as the sodium salt of GHB, sodium oxybate, are extremely hygroscopic. As used herein, the term "hygroscopic" is used to describe a substance that readily absorbs and attracts water from the surrounding environment. The hygroscopic nature of sodium oxybate presents significant challenges to the formulation, production, and storage of dosage forms capable of delivering sodium oxybate over a sustained period of time. Despite the challenges noted, formulations and unit dosage forms providing controlled release of GHB are described herein.

A. Controlled Release Formulations

As used herein, the term "controlled release" describes a formulation, such as, for example, a unit dosage form, that releases drug over a prolonged period of time. The controlled release compositions described herein may be provided as a unit dosage form suitable for oral administration. In each embodiment of the controlled release compositions described herein, the drug incorporated in such compositions may be selected from GHB and pharmaceutically acceptable salts, hydrates, tautomers, solvates and complexes of GHB.

In certain embodiments, the controlled release compositions described herein are formulated as unit dosage forms that deliver therapeutically effective amounts of drug over a period of at least 4 hours. For example, controlled release unit dosage forms as described herein may be formulated to deliver therapeutically effective amounts of drug over a period selected from about 4 to about 12 hours. In specific embodiments, the controlled release dosage forms described herein deliver therapeutically effective amounts of drug over a period selected from about 4, about 5, about 6, about 7, about 8, about 9, about 10 hours, and about 12 hours. In other such embodiments, the controlled release dosage forms deliver therapeutically effective amounts of drug over a period selected from a range of about 4 to about 10 hours, about 5 to about 10 hours, about 5 to about 12 hours, about 6 to about 10 hours, about 6 to about 12 hours, about 7 to about 10 hours, about 7 to about 12 hours, about 8 to about 10 hours, and from about 8 to about 12 hours. In yet other embodiments, the controlled release dosage forms deliver therapeutically effective amounts of drug over a period selected from a range of about 5 to about 9 hours, about 5 to about 8 hours, about 5 to about 7 hours, and about 6 to about 10 hours, about 6 to about 9 hours, and about 6 to about 8 hours.

The compositions described herein facilitate production of controlled release dosage forms that provide a substantially constant drug release rate. In one embodiment, the controlled release dosage forms may be formulated to deliver not more than approximately 30% of the drug initially contained within the controlled release dosage form in the first hour post-administration. When referencing the amount of drug initially contained in the controlled release dosage form or "initial drug content" of the controlled release dosage form, for purposes of the present description, such amount refers to the total amount of drug included in the controlled release composition prior to administration to a patient.

As is detailed herein, the controlled release dosage forms according to the present description include a controlled release component (also referred to as a controlled release "formulation") and, optionally, an immediate release component (also referred to as an immediate release "formulation" or an immediate release "coating"). In specific embodiments, the controlled release dosage forms described herein may be formulated to deliver drug to the gastro-intestinal tract at desired rates of release or release profiles. For example, in some embodiments, controlled release dosage forms as described herein are formulated to release to the gastro-intestinal tract not more than about 10% to about 60% of the drug initially contained within the controlled release component of the controlled release dosage form during the first two hours post-administration, and not more than about 40% to about 90% of the drug initially contained within the controlled release component of the controlled release dosage form during the first four hours post-administration. In other embodiments, controlled release dosage forms as described herein are formulated to release to the gastro-intestinal tract not more not more than about 40% of the drug initially contained within the controlled release component in the first hour post-administration, not more than about 60% of the drug initially contained within the controlled release component during the first two hours post-administration, and not more than about 90% of the drug initially contained within the controlled release component during the first four hours post-administration. In still other embodiments, a controlled release dosage form as described herein may be formulated to release to the gastro-intestinal tract not more than about 30% of the initial drug content in the controlled release component in the first hour post-administration, not more than about 60% of the initial drug content in the controlled release component during the first two hours post-administration, and not more than about 90% of the initial drug content of the controlled release component during the first four hours post-administration. In other embodiments, a controlled release dosage form as described herein may be formulated to release to the gastro-intestinal tract not more than about 50% of the initial drug content of the controlled release component during the first hour post-administration, between about 50 and about 75% of the initial drug content of the controlled release component after two hours, and not less than 80% of the initial drug content of the controlled release component after four hours post administration. In still other embodiments, a controlled release dosage form as described herein may be formulated release to the gastro-intestinal tract not more than about 20% of the initial drug content of the controlled release component during the first hour post-administration, between about 5 and about 30% of the initial drug content of the controlled release component after two hours, between about 30% and about 50% of the initial drug content of the controlled release component after 4 hours, between about 50% and about 70% of the initial drug content of the controlled release component after 6 hours, and not less than about 80% of the initial drug content of the controlled release component after 10 hours post administration. In yet other embodiments, a controlled release dosage form as described herein may be formulated to release to the gastro-intestinal tract not more than about 20% of the initial drug content of the controlled release component after the first hour post-administration, between about 20% and about 50% of the initial drug content of the controlled release component after 2 hours, between about 50% and about 80% of the initial drug content of the controlled release component after 4 hours, and not less than 85% of the initial drug content of the controlled release component after 8 hours post-administration. The rate and extent of the absorption of GHB varies along the length of the GI tract with lower amounts absorbed in the more distal portions (i.e., the ileum and the colon).

Due to the rapid clearance of GHB from the plasma, when GHB is administered in an immediate release formulation, even large doses of the drug (e.g., a dose of between about 2.25 g and 4.5 g) generally result in plasma levels below 10 ug/mL within 4 hours of ingestion. In order to achieve therapeutic efficacy, therefore, a second, equal, dose is often required within 4 hours after administration of the first dose, and some patients may require administration of a second as soon as 2.5 hours after administration of the first dose. In such an instance, in order to maintain therapeutic efficacy, 4.5 g to 9 g of drug must be administered to the patient in two separate doses within 2 to 5 hours. This also requires that the second dose be administered during the night, which requires that the patient be awakened to take the second dose. The result is that the Cmax/Cmin ratio of GHB over an six hour period can be greater than 4 and is often greater than 8. In certain embodiments, for a given dose of GHB, administration of GHB using controlled release dosage forms as described herein can achieve a rapid rise in plasma concentrations of GHB, but with a prolonged duration of plasma levels above 10 µg/mL. In certain such embodiments, a GHB controlled release dosage form as described herein provides a Cmax to Cmin ratio of GHB over a prolonged period of time after administration selected from less than 3 and less than 2. Therefore, in specific embodiments, the controlled release dosage forms described herein provided controlled delivery of GHB that results in a Cmax to Cmin ratio of GHB selected from less than 3 and less than 2 over a period of time selected from up to about 5 hours, up to about 6 hours, up to about 7 hours, up to about 8 hours, up to about 9 hours, and up to about 10 hours. For example, in particular embodiments, the controlled release dosage forms described herein provided controlled delivery of GHB that results in a Cmax to Cmin ratio of GHB selected from less than 3 over a period of time selected from up to about 5 hours, up to about 6 hours, up to about 7 hours, up to about 8 hours, up to about 9 hours, and up to about 10 hours, while also providing GHB plasma concentrations of at least 10 µg/mL over a period of time selected from up to about 5 hours, up to about 6 hours, up to about 7 hours, up to about 8 hours, up to about 9 hours, and up to about 10 hours. In still other embodiments, the controlled release dosage forms described herein provided controlled delivery of GHB that results in a Cmax to Cmin ratio of GHB selected from less than 2 over a period of time selected from up to about 5 hours, up to about 6 hours, up to about 7 hours, up to about 8 hours, up to about 9 hours, and up to about 10 hours, while also providing GHB plasma concentrations of at least 10 µg/mL over a period of time selected from up to about 5 hours, up to about 6 hours, up to about 7 hours, up to about 8 hours, up to about 9 hours, and up to about 10 hours.

Drug delivery performance provided by the dosage forms described herein can be evaluated using a standard USP type 2 or USP type 7 dissolution apparatus set to 37° C.±2° C. under the conditions described, for example, in the experimental examples provided herein. The dissolution media may be selected from dissolution media known by those of skill in the art such as at least one of purified water, 0.1N HCl, simulated intestinal fluid, and others.

In particular embodiments, the controlled release formulations described herein work to reduce inter patient variability in delivery of GHB. In particular, controlled release formulations described herein provide time dependent release of GHB over a sustained period of time. Previous references have described targeted release dosage forms of GHB that function in a pH dependent manner. However, due to inter-subject variability in gastrointestinal pH conditions, delivery of GHB from such dosage forms can be inconsistent. Moreover, because relatively high doses of GHB are typically required for therapeutic effect, unit dosage forms of GHB are also relatively large and may be retained for a period of time in the stomach, which can lead to intra- and inter-patient variability in dose delivery of GHB from pH dependent delivery systems due to variability in gastric retention time. Further, patients with fibromyalgia have an increased chance of also suffering from irritable bowel syndrome (see, e.g., Fibromyalgia in patients with irritable bowel syndrome. An association with the severity of the intestinal disorder, Int J Colorectal Dis. 2001 August; 16(4): 211-5.) Irritable bowel syndrome is also associated with delayed gastric emptying and variable gastric emptying (see, e.g., Dyspepsia and its overlap with irritable bowel syndrome, Curr Gastroenterol Rep. 2006 August; 8(4):266-72.) Therefore many patients with fibromyalgia and suffering from irritable bowel syndrome may experience more variability in gastric transit or prolonged gastric transit. By operating in a time dependent manner once placed in an aqueous environment, controlled release formulations described herein offer consistent GHB delivery characteristics and reduce the likelihood of undesirable intra- and inter-patient inconsistencies in dose delivery that may result from variances in gastric retention time that can occur between different patients and different patient populations.

Controlled release formulations described herein may be formulated to completely release a drug within a desired time interval. As has been reported, the bioavailability of GHB decreases in the lower GI, with bioavailability decreasing the lower the drug is delivered in the GI (See, e.g., U.S. Patent Publication No. US2006/0210630). Therefore, in certain embodiments, the controlled release dosage forms are provided that deliver substantially all the GHB contained therein over a sustained period of time that is long enough to increase patient convenience, yet short enough to reduce dosing of GHB in the lower GI. In specific embodiments, controlled release GHB dosage forms are provided that deliver approximately 90% or more of the GHB contained within the controlled release formulation within about 4 to about 10 hours of administration. For example, dosage forms for the controlled release of GHB as described herein may be formulated to deliver approximately 90% or more of the drug included within the controlled release formulation within about 4, 5, 6, 7, 8, 9, 10, or 12 hours of administration. In one such embodiment, a dosage form for the sustained delivery of GHB according to the present description is formulated to deliver more than 90% of the GHB included within the controlled release formulation within 12 hours post-administration. Such embodiments serve to not only provide controlled release of GHB, but they also work to deliver GHB where bioavailability is highest, which can also provide increased dose consistency.

The controlled release dosage forms described herein may comprise a relatively high concentration of drug that can, in some instances, harm a patient if the formulation releases the drug at a rate that is faster than the intended sustained rate. This rapid release of the drug is sometimes referred to as "dose dumping." To avoid this potential danger, certain embodiments of the controlled release dosage forms described herein may comprise formulations that are resistant to dose dumping. Some users may intentionally attempt to increase the drug release rate of the controlled release dosage form using alcohol (e.g., potential abusers may take the controlled release dosage form prior to, simultaneously with, or after consuming an alcoholic beverage or, alternatively, may seek to extract the drug from the controlled release dosage form by placing the dosage form in solution containing alcohol). Other users may take the dosage form with alcohol, not necessarily in a manner considered abuse of the drug or alcohol, but without regard for the potential risks of dose dumping or contraindication of the two substances. In one embodiment, a controlled release dosage form as disclosed herein may include a coating composition that is resistant to alcohol or that does not dissolve substantially faster in alcohol. In one such embodiment, the controlled release dosage form may comprise the drug sodium oxybate and include a coating composition including ethylcellulose that is resistant to dose dumping in alcohol. In another embodiment, the controlled release dosage form may include a coating composition that is resistant to dose dumping after administration. For example, the controlled release dosage form may include a coating composition that is resistant to dose dumping in the GI tract after being exposed to gastric fluid and intestinal fluid.

In certain embodiments, the controlled release formulations described herein are provided as a coated tablet composition having a controlled release core coated by a functional overcoat. The composition of the controlled release core provided in such embodiments facilitates high drug loading, thereby, rendering the coated tablet suitable for formulation and sustained delivery of drugs administered at high doses. The functional overcoat works to control delivery of drug from the controlled release core and maintain the structural integrity of the dosage form over time. In addition to the controlled release core and functional overcoat, the coated tablet composition as described herein may further include a moisture barrier or cosmetic coating disposed over the functional overcoat.

I. Controlled Release Component

Where the controlled release formulations described herein are formulated as a coated tablet having a controlled release core (CR core), the CR core includes at least one drug substance to be delivered from the controlled release dosage form. The drug included in the CR core may be selected from GHB and pharmaceutically acceptable salts, hydrates, tautomers, solvates and complexes of GHB. Examples of suitable salts of GHB include the calcium, lithium, potassium, sodium and magnesium salts. The CR core is formulated and configured to be suitable for oral administration. In one embodiment, coated tablets as described herein may be administered to provide a dose of GHB or a pharmaceutically acceptable salt, hydrate, tautomer, solvate or complex of GHB in a range of about 500 mg to about 12 g of drug in one or more tablets. In particular embodiments, a CR core included in a controlled release dosage form according to the present description may include an amount of drug selected from about 100 mg to about 2,000 mg. In some such embodiments, the amount of drug included in the CR core may be selected from up to about 250 mg, 400 mg, 500 mg, 600 mg, 700 mg, 750 mg, 800 mg, 900 mg, 1,000 mg, 1,100 mg, 1,200 mg, 1,400 mg, 1,500 mg, 1,600 mg, 1,700 mg, 1,800 mg, 1,900 mg, and 2,000 mg. In certain such embodiments, the amount of drug included in a CR core as described herein may range from about 500 mg to about 2,000 mg, such as, for example, about 500 mg to 1,000 mg, about 600 mg to 1,000 mg, about 600 mg to 900 mg, about 600 mg to 800 mg, about 700 mg to 1,000 mg, about 700 mg to 900 mg and about 700 mg to 850 mg. In other such embodiments, the amount of drug included in a CR core as described herein may range from about 700 mg to about 2,000 mg, such as, for example, about 700 mg to 1,500 mg, about 700 mg to 1,400 mg, about 700 mg to 1,300 mg, about 700 mg to 1,200 mg, about 700 mg to 1,100 mg, about 700 mg to 1,000 mg, about 700 mg to 900 mg, and about 700 mg to 850 mg.

In one embodiment, the controlled release dosage form comprises a CR core wherein the relative amount drug in the CR core is at least 90% or greater by weight. In another embodiment, the relative amount of drug in the CR core ranges from between about 90% and 98%, about 91% and 98%, about 92% and 98%, about 93% and 98%, about 94% and 98%, about 95% and 98%, about 96% and 98%, and between about 97% and 98% by weight of the CR core. In yet another embodiment, the relative amount of drug in a CR core may be present at an amount selected from about 90%, 91%, 92%, 93%, 94%, 95%, 96%, 97%, and 98% by weight of the CR core. In certain such embodiments, the amount of drug in the CR core may range from about 94 to 98%, 94 to 97%, 94 to 96%, 95 to 98%, 95 to 97%, and 95 to 96.5 by weight of the CR core.

In one embodiment, the controlled release dosage form comprises a CR core that includes drug substance in combination with one or more excipients, such as binders, fillers, diluents, disintegrants, colorants, buffering agents, coatings, surfactants, wetting agents, lubricants, glidants, or other suitable excipients. In one embodiment, a CR core as disclosed herein can include one or more binders that are known for use in tablet formulations. In one such embodiment, a CR core may include at least one binder selected from hydroxypropyl cellulose (HPC), ethylcellulose, hydroxypropyl methylcellulose (HPMC), hydroxyethyl cellulose, povidone, copovidone, pregelatinized starch, dextrin, gelatin, maltodextrin, starch, zein, acacia, alginic acid, carbomers (cross-linked polyacrylates), polymethacrylates, carboxymethylcellulose sodium, guar gum, hydrogenated vegetable oil (type 1), methylcellulose, magnesium aluminum silicate, and sodium alginate. In specific embodiments, the CR core included in a controlled release dosage form as disclosed herein may comprise binder levels ranging from approximately 1% to 10% by weight. For example, the CR core may include a binder in an amount selected from about 1%, 1.5%, 2%, 2.5%, 3%, 3.5%, 4%, 4.5%, 5%, 6%, 7%, 8%, 9%, and 10% by weight. In certain such embodiments, the amount of binder included in the CR core may range from about 1 to 2%, 1 to 3%, 1 to 4%, 1 to 5%, 1 to 6%, 1 to 7%, 1 to 8%, 1 to 9% and 1 to 10% by weight.

The CR core may include one or more lubricants to improve desired processing characteristics. In one embodiment, the CR core may include one or more lubricants selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate. In another embodiment, one or more lubricants may be added to the CR core in a range of about 0.5% to 5% by weight. In particular embodiments, a CR core as disclosed herein may comprise a lubricant in a range of about 0.5% to 2% by weight, about 1% to 2% by weight, about 1% to 3% by weight, about 2% to 3% by weight, and about 2% to 4% by weight. In one such embodiment, one or more lubricants may be present in the CR core in an amount selected from about 0.5%, 1%, 1.5%, 2%, 2.5%, 3%, 3.5%, 4%, 4.5%, and 5% by weight. Still lower lubricant levels may be achieved with use of a "puffer" system during tabletting, which applies lubricant directly to the punch and die surfaces rather than throughout the formulation.

The CR core may also include one or more surfactants. In certain embodiments, the CR core may include a tableted composition that may comprise one or more surfactants selected from, for example, ionic and non-ionic surfactants. In one such embodiment, CR core may include at least one anionic surfactant, including docusate sodium (dioctyl sulfosuccinate sodium salt) and sodium lauryl sulfate. In yet another embodiment, the CR core may include at least one non-ionic surfactant selected from including polyoxyethylene alkyl ethers, polyoxyethylene stearates, poloxamers, polysorbate, sorbitan esters, and glyceryl monooleate. In specific embodiments, one or more surfactants included in a CR core as disclosed herein may be present, for example, in an amount of up to about 3.0% by weight of the CR core. For example, in certain embodiments, the CR core may include one or more surfactants present in a range selected from about 0.01% to 3%, about 0.01% to 2%, about 0.01% to 1%, about 0.5% to 3%, about 0.5% to 2%, and about 0.5% to 1% by weight of the CR core.

The CR core included in controlled release dosage form as disclosed herein may also include fillers or compression aids selected from at least one of lactose, calcium carbonate, calcium sulfate, compressible sugars, dextrates, dextrin, dextrose, kaolin, magnesium carbonate, magnesium oxide, maltodextrin, mannitol, microcrystalline cellulose, powdered cellulose, and sucrose. In another embodiment, a CR core may be prepared by blending a drug and other excipients together, and the forming the blend into a tablet, caplet, pill, or other dosage form according to methods known by those of skill in the art. In certain embodiments, a controlled release formulation as described herein may comprise a solid oral dosage form of any desired shape and size including round, oval, oblong cylindrical, or triangular. In one such embodiment, the surfaces of the CR core may be flat, round, concave, or convex.

The CR core composition included in a controlled release formulation provided as a coated tablet dosage form as described herein may be manufactured using standard techniques, such as wet granulation, roller compaction, fluid bed granulation, and direct compression followed by compression on a conventional rotary tablet press as described in Remington, 20$^{th}$ edition, Chapter 45 (Oral Solid Dosage Forms).

II. Functional Coating Composition

Where the controlled release formulations as described herein are provided as a coated tablet composition, the CR core is coated with a functional coating. The coating composition works to preserve the integrity of the unit dosage form post administration and serves to facilitate controlled release of drug from the CR core. In certain embodiments, the coating composition is formulated to facilitate controlled release of a drug selected from GHB and pharmaceutically acceptable salts, hydrates, tautomers, solvates and complexes of GHB. In one such embodiment, the coating composition is sufficiently robust to preserve the integrity of the coated tablet pre- and post-administration, yet is subject to disintegration or crushing as it passes through a patient's gastrointestinal tract and after all or substantially all the drug substance contained within the controlled release formulation has been delivered. Such a feature reduces the risk that bezoars formed from intact dosage form shells will form or be maintained within the GI tract of a patient, which may be of particular concern where the drug to be delivered must be administered at high doses using multiple unit dosage forms.

In one embodiment, a functional coating composition as disclosed herein may control, at least in part, the rate of release of the drug to be delivered from the CR core into the gastrointestinal tract. In one embodiment, the functional coating composition provides a functional coat that partly or fully covers the CR core included in the controlled release dosage form. In one embodiment, the functional coating composition as disclosed herein may include a polymer or blends of compatible polymers that are water soluble or that are water insoluble and selected to exhibit desired permeability characteristics. In one embodiment, the functional coating composition has a permeability that may be adjusted according the solubility of the drug used in the CR core. In one such embodiment, the functional coating composition may comprise one or more water insoluble polymers that may swell but do not substantially dissolve in the GI tract. For example, in particular embodiments, a functional coating composition as disclosed herein may comprise a rate-limiting film that includes at least one of ethylcellulose, cellulose acetate, such as CA-398. In other embodiments, the functional coating may include combinations of ethylcellulose with ammonio methacrylate copolymers, such as EUDRAGIT RS, EUDRAGIT RL, and combinations thereof. Suitable ethylcellulose materials are readily commercially available, and include, for example, ETHOCEL ethylcellulose polymers. Where ethylcellulose is used to form the functional coating, the physical characteristics of the coating composition and residual shell may be modified by adjusting the molecular weight of the ethylcellulose. For example, different grades of ethylcellulose, including, but not limited to, 4 cP, 7 cP, 10 cP, and 20 cP grades, may be used to achieve a coating composition having desired physical characteristics.

A functional coating composition as disclosed herein may include one or more base polymer and at least one pore-former. In one embodiment, the base polymer content may range from about 50% to about 80% by weight of the coating composition. In certain embodiments, the base polymer may be present in an amount ranging from about 50% to 75%, about 55% to 75%, about 60% to 75%, and about 65% to 75% by weight of the coating composition. In one such embodiment, the base polymer may be present in an amount selected from about 50%, 55%, 60%, 65%, 70%, 75%, and 80% by weight of the coating composition. In cases where a filler material is used (e.g., insoluble, non film-forming material such as magnesium stearate, talc, or fumed silica), these limits apply to the composition of the remaining non-filler components in the film.

The permeability of the base polymer included in a functional coating as described herein may be modified by including a pore former in the base polymer. In one embodiment, the functional coating composition including the pore former may be obtained by combining the pore former with the base polymer material in solution according to conventional techniques. A pore former as disclosed herein may include at least one polymeric pore former, such as hydroxyalkyl cellulose, hydroxypropyl methylcellulose, hydroxypropyl cellulose, polyethylene glycols, polyvinyl alcohol, povidone, copovidone, and poloxamers, such as 188 or 407. In one embodiment, a pore former as disclosed herein may include at least one small-molecule pore former, such as a water soluble sugar or organic acid, including, for example, citric acid or sorbitol. In one such embodiment, a small-molecule pore former may be water soluble active agent, such as a pharmaceutically acceptable salt of GHB. In yet another embodiment, the pore former may comprise a polymer that expands in the presence of the drug included in the CR core, wherein expansion of the pore former may cause an increase in permeability of the functional coating composition. For example, in some embodiments, the functional coating composition may comprise a pore former that that expands or swells in the presence of sodium oxybate. In one such embodiment, the pore former includes a suitable carbomer.

Where used in the functional coating composition, a pore former or a pore-forming agent can be selected to modify the permeability of the coating composition provided over the CR core. For example, the permeability of the functional coating composition may be increased by including one or more pore formers or pore-forming agents in the coating composition. In one embodiment, the pore formers disclosed herein may be soluble in water. In one such embodiment, when a CR dosage form comprising a functional coating composition with at least one pore former is swallowed by a patient and contacted with gastric fluid, the water-soluble pore formers may dissolve and form pores or channels in the coating through which the drug is released. It is possible to use an enteric component as part or all of the pore former in the coating composition. Examples of such materials that may be used as a pore former in the context of the present description include cellulose acetate phthalate, methacrylic acid-methyl methacrylate copolymers, and polyvinyl acetate phthalate. However, incorporating enteric components in the film may result in delivery characteristics that exhibit some level of sensitivity to gastric and intestinal transit times.

Where included, the amount and nature of the pore former included in the functional coating composition can be adjusted to obtain desired release rate characteristics for a given drug substance. In one embodiment, the functional coating composition may include an amount of pore former that ranges from about 20% to about 50% by weight of the coating composition. For example, the pore former may be present in an amount ranging from about 20% to 45%, about 25% to 45%, about 30% to 45%, and about 35% to 45% by weight of the functional coating composition. In one such embodiment, the pore former may be present in an amount selected from about 20%, 25%, 30%, 35%, 40%, 45%, and 50% by weight of the functional coating composition.

The functional coating composition as disclosed herein may also comprise one or more plasticizers. In certain embodiments, the functional coating composition may include a plasticizer such as triethyl citrate or dibutyl sebacate. In one such embodiment, a plasticizer may be present in the functional coating composition in an amount ranging from about 5% to 15% by weight relative to the base polymer. In certain embodiments, the functional coating composition may include a plasticizer in an amount selected from about 5%, 8%, 10%, 12%, and 15% by weight relative to the base polymer.

The functional coating composition as disclosed herein may also include an anti-tack agent. For example, certain embodiments of the functional coating composition may include an anti-tack agent selected from one or more of talc, glyceryl monostearate, and magnesium stearate. Many of the anti-tack agents are also suitable fillers. Addition of fillers, especially magnesium stearate, is one way to make the film more brittle and the dosage form more prone to crushing as it transits through the GI. Depending on forces encountered in the GI, varying the filler level in the film may allow one to adjust the duration, or extent of drug delivered, at which breach of the film and abrupt release of remaining contents occurs.

The functional coating composition as disclosed herein may be applied to a CR core at a weight that facilitates a suitable combination of sustained drug release and dosage form structural integrity. In certain embodiments, the functional coating composition may be applied at a weight of about 10 to about 100 mg. In particular embodiments, for example, the functional coating may be applied at a weight selected from about 20 to 60 mg, about 20 to 50 mg, about 20 to 40 mg, about 20 to 30 mg, about 30 to 60 mg, about 30 to 50 mg, about 30 to 40 mg, about 40 to 60 mg, about 40 to 50 mg, and about 50 to 60 mg. These ranges are useful for oval tablets of about 500 mg to about 1000 mg in weight. Alternatively, for a given tablet size or weights, the functional coating composition as disclosed herein may be applied at between about 2.5% and 7.5% of the tablet weight. For example, in one such embodiment, where the tablet is a 2,000 mg oval tablet, a functional coating composition may be applied at a weight ranging from about 50 mg to about 150 mg.

In addition to adjusting the amount or nature of the pore former included in the functional coating composition, the release rate of drug provided by the controlled release dosage form disclosed herein may be adjusted by modifying the thickness or weight of the functional coating composition. For example, a more rapid release rate will generally be achieved as the amount of a given pore former included in the functional coating composition is increased or the thickness or weight of the coating composition applied over the CR core is decreased. Conversely, a slower or more controlled release may be achieved, generally, as relatively less of a given pore former is included in the functional coating composition or the thickness or weight of the coating composition applied to the CR core is increased. Additionally, in certain embodiments, the release rate of drug from the CR core may be adjusted by modifying the water content of the functional coating composition. For example, increasing the water content of the functional coating composition may increase the release rate of drug the CR core.

The functional coating compositions as disclosed herein may be applied to a CR core according to conventional coating methods and techniques. In one embodiment, the functional coating composition as disclosed herein may be applied using a conventional perforated pan coater. In another embodiment, the functional coating composition may be applied using an aqueous pan-coating process. In one such embodiment, the use of an aqueous pan-coating process may include the use of a latex dispersion. For example, a latex dispersion such as SURELEASE may be used for an ethylcellulose pan-coating process. In another example, a latex dispersion such as EUDRAGIT RS 30 D may be used in a pan-coating process for ammonio-methacrylates. In yet another embodiment, the functional coating composition may be applied using a solvent-based pan-coating process. In one such embodiment, a solvent-based pan-coating process may include the use of an alcohol solvent, such as ethanol. For example, an alcohol-solvent based pan-coating process may utilize a 95% ethanol and 5% water (w/w) solvent.

In one embodiment, the functional coating compositions as described herein may be applied using a fluid bed coating process such as a Wurster fluid bed film coating process. In another embodiment, the functional coating composition may be applied using a compression coating process. In yet another embodiment, the functional coating composition may be applied using a phase inversion process. In certain embodiments, the functional coating composition as disclosed herein may be applied over a suitable subcoating.

III. Moisture Barrier/Cosmetic Coatings

When a controlled release formulation or dosage form is provided as a coated tablet, in some embodiments, it may be coated with a moisture barrier or a moisture-resistant coating composition. For example, a controlled release dosage form as disclosed herein comprising GHB as the drug substance may include a moisture barrier. In another example, a moisture barrier may be particularly useful where sodium oxybate is used as the drug substance. In one embodiment, the moisture barrier may be a polyvinyl alcohol-based coating, such as OPADRY AMB (Colorcon Inc., Harleysville, Pa.). In another embodiment, the moisture barrier may be a hydroxypropyl methylcellulose (HPMC)/wax-based coating, such as AQUARIUS MG (Ashland Aqualon, Wilmington, Del.). In yet another embodiment, the moisture barrier may be a HPMC/stearic acid-based coating. The moisture barrier as disclosed herein, in some embodiments, may be formed using a reverse enteric material, such as EUDRAGIT E, and may be coated from alcohol or alcohol/water solutions or from an aqueous latex dispersion. In embodiments where the controlled release dosage form is provided as a tablet of about 500 mg-1000 mg in weight, for example, the moisture barrier coating may be applied at a weight selected from about 10 mg to about 60 mg/tablet and about 25 mg to about 50 mg/tablet. In general, a minimum weight is needed to ensure complete coverage of the tablet in light of imperfections in the tablet surface, and a maximum weight is determined by practical considerations, such as coating time, or by the need for better moisture protection.

As will be readily appreciated, the controlled release dosage form can be further provided with a cosmetic top coat. In one embodiment, a top-coat may be applied to an existing coating composition such as a moisture barrier. In certain embodiments, a cosmetic top-coat may include at least one of HPMC and copovidone. For example, when the controlled release dosage form includes a coated tablet comprising sodium oxybate as the drug, a top-coat including HPMC, such as for example an HPMC material selected from one or more of HPMC E3, E5, or E15, may be applied over a moisture barrier to improve the effectiveness of the moisture barrier by reducing any seepage of sodium oxybate and water from the surface of the coated tablet.

B. Immediate Release Formulations

The controlled release formulations described herein can be dosed together with an immediate release (IR) formulation. In one embodiment, the IR formulation may be provided as a separate formulation or dosage form that may be dosed together with a dosage form provided by a controlled release dosage form as described herein. The IR formulation may be provided in any suitable form, such as a dry powder formulation, a tablet or capsule unit dosage form, or a liquid formulation such as a solution or suspension formulation. As used herein, "immediate release" refers to a drug formulation that releases more than about 95% of the drug contained therein within a period of less than one hour after administration. In particular embodiments, the IR component of the compositions described herein release more than about 95% of the drug contained therein within a period selected from less than 45 minutes, less than 30 minutes, and less than 15 minutes post-administration. In other embodiments, the IR component of the compositions described herein release more than about 80% of the drug contained therein within a period selected from less than 45 minutes, less than 30 minutes, and less than 15 minutes post-administration.

In certain embodiments, the IR formulation is provided as an immediate release component of a controlled release dosage form as described herein. In one such embodiment, the IR component is provided as a coating over a controlled release component or formulation as described herein. A unit dosage form that integrates both controlled release and immediate release components can increase the convenience and accuracy with which a drug such as GHB is dosed to patients by providing a unit dosage form that not only provides quick onset of action, but also sustained delivery of GHB to the patient over a prolonged period of time. Furthermore, where the drug to be delivered is selected from GHB and pharmaceutically acceptable salts, hydrates, tautomers, solvates and complexes of GHB, dosing controlled release and immediate release formulations together may avoid the disadvantages of the current GHB dosing regimens, which can result in highly pulsatile plasma concentrations.

I. Immediate Release Component

When the immediate release formulation is provided as an integrated IR component of a controlled release dosage form, the amount of drug included in the IR component may range from about 10% to 50% by weight of the total drug included in the integrated dosage form. As used herein, "integrated dosage form" refers to a single unit dosage form that includes both immediate release and controlled release components as described herein. For example, where the drug to be delivered from the immediate release and controlled release formulations incorporated into an integrated dosage form is selected from GHB and pharmaceutically acceptable salts, hydrates, tautomers, solvates and complexes of GHB in some embodiments, the drug included in the IR component may comprise about 10% to about 50% by weight of the total drug included in the unit dosage form. In one such embodiment, the drug included in the IR component of an integrated dosage form may comprise about 10%, 15%, 20%, 25%, 30%, 35%, 40%, 45%, or 50% by weight of the total drug included in the unit dosage form. For example, an integrated dosage form as described herein may contain 1000 mg sodium oxybate, wherein 100 mg to 500 mg sodium oxybate (10% to 50% by weight) is contained within and delivered from the IR component and 500 mg to 900 mg sodium oxybate (50% to 90% by weight) is contained within and delivered from the CR component.

Where the IR component is provided as a coating over a controlled release dosage form, in certain embodiments, the drug included in the IR component may account for between about 75% and 98% by weight of the IR formulation. In the context of describing an IR component provided over a controlled release dosage form as described or disclosed herein, the controlled release dosage forms referred to include the controlled release formulations described herein, including, in specific embodiments, CR cores coated with a functional coating as described herein. Again, the drug included in such an embodiment may be selected from GHB and pharmaceutically acceptable salts, hydrates, tautomers, solvates and complexes of GHB. In certain embodiments, the IR component may comprise sodium oxybate in an amount of selected from a range of between about 75% and 98%, between about 80% and 98%, between about 85% and 98%, between about 90% and 98%, and between about 95% and 98% by weight.

An IR component formed as a coating over a controlled release dosage form as disclosed herein may be applied as a tableted overcoat according to conventional tablet coating and binding methods. Alternatively, an IR component formed as a coating over a controlled release dosage form as disclosed herein may be applied as a film coating, such as, for example, from a solution containing a suitable amount of drug and film former. In one such embodiment, wherein sodium oxybate is the drug included in the IR component, the coating forming the IR component may be coated over a controlled release dosage form from a coating solution that utilizes an alcohol and water solvent. For example, a suitable immediate release coating may be formed using a 20% solution of sodium oxybate in a 60%/40% (w/w) alcohol/water solution that contains a suitable film-former.

Where the IR component is provided as a film coat and includes one or more film-formers, suitable film formers may be selected from, for example, copovidone, hydroxypropyl cellulose, HPMC, and hydroxymethyl cellulose materials. An IR component containing sodium oxybate as the drug can be applied as a suspension or as a solution by adjusting the water content of the coating mixture. For a suspension, little or no water is added to the alcohol, and the example film formers should be suitable. To prepare a solution, however, the water content of the solvent is increased, for example to 40%, and a smaller set of film formers would be suitable due to the precipitation of most common film formers in the presence of sodium oxybate solution. Hypromellose is one of several potential film formers that is suitable. It is further possible, with more difficulty, to apply the sodium oxybate from an aqueous solution; however, the same limitations on film former applies, and processing is complicated by the hygroscopic nature of the drug. In one embodiment, the IR component useful for use in a controlled release dosage form as described herein includes 91% sodium oxybate and 9% hypromellose (HPMC E-15) that is applied from a solution containing 20% sodium oxybate and 2% HPMC E-15 in a 60/40 w/w ethanol/water solvent.

Where the IR component of an integrated dosage form is provided as a coating over the controlled release dosage form, the coating forming the IR component may further include one or more of an anti-tack agent and a plasticizer to facilitate processing and to improve film properties. Furthermore, addition of one or more surfactants, such as sodium lauryl sulfate, may improve the dissolution of IR coatings that contain hydrophobic components (such as anti-tack agents or water-insoluble film formers).

In embodiments where the IR component is provided as a coating over a controlled release formulation as described herein, the IR component may be positioned directly over the functional coating of the controlled release formulation. Where desired or necessary based on the drug to be delivered from the IR component and controlled release formulation included in such an integrated dosage form, the outer surface of the IR component may then be coated with a moisture barrier layer. For example, where the drug delivered by the integrated dosage form is highly hygroscopic, such as, for example, sodium oxybate, a moisture barrier layer over the immediate release coating forming the IR component may be provided.

The formulation and structure of integrated dosage forms as described herein can be adjusted to provide a combination of immediate release and controlled release performance that suits a particular dosing need. In particular, the formulation and structure of integrated dosage forms as described herein can be adjusted to provide any combination of the immediate release and controlled release performance characteristics described herein. In particular embodiments, for example, the drug delivered from an integrated dosage form as described herein is selected from GHB and pharmaceutically acceptable salts, hydrates, tautomers, solvates and complexes of GHB, and the integrated dosage form sustains delivery of GHB over a period of from about 4 to about 10 hours. In one such embodiment, the IR component of the integrated dosage form provides rapid onset of action, releasing more than about 90% of the drug contained therein within a period of time selected from less than one hour, less than 45 minutes, less than 30 minutes and less than 15 minutes after administration, while the controlled release composition included in the integrated dosage begins to deliver drug as the IR component is released and continues to deliver drug for a sustained period of between about 4 and about 10 hours. In another such embodiment, the IR component of the integrated dosage form provides rapid onset of action, releasing more than about 90% of the drug contained therein within a period of time selected from less than one hour, less than 45 minutes, less than 30 minutes and less than 15 minutes after administration, while the controlled release composition included in the integrated dosage begins to deliver drug after the IR component is released and continues to deliver drug for a sustained period of between about 4 and about 10 hours.

Moreover, the ratio of drug release from the IR component and CR component can be adjusted as needed to facilitate a desired dosing regimen or achieve targeted dosing. A dosage form as described herein that integrates both IR and CR components may be formulated to deliver as much as 2,000 mg of a desired drug, such as GHB or a pharmaceutically acceptable salt, hydrate, tautomer, solvates or complex of GHB. In particular embodiments, the total amount of drug contained within an integrated IR/CR dosage form according to the present description may be between about 500 mg and about 1,400 mg. For example, in certain such embodiments, the total amount of drug may be selected from between about 500 mg and 1,400 mg, about 500 mg and 1,200 mg, about 500 mg and 1,100 mg, about 600 mg and 1,200 mg, about 600 mg and 1,100 mg, about 600 mg and 1,000 mg, about 600 mg and 950 mg, about 600 mg and 850 mg, about 600 mg and 750 mg, about 750 mg and 1,200 mg, about 750 mg and 1,100 mg, about 750 mg and 1,000 mg, about 750 mg and 950 mg, and about 750 mg and 850 mg. In an integrated IR/CR dosage form, the relative amounts of drug delivered from the IR component and CR components may be adjusted as desired as well. In particular embodiments, the ratio of drug released from the IR component to drug released from the CR component is from about 1:2 to about 1:4. In certain embodiments, such ratio is selected from about 1:2, 1:2.5, 1:3, 1:3.5 and 1:4.

In particular embodiments, the integrated dosage form may be formulated such that the controlled release formulation begins release of drug substantially simultaneously with delivery of the drug from the IR component. Alternatively, the integrated dosage form may be formulated such that controlled release formulation exhibits a start-up time lag. In one such embodiment, for example, the integrated dosage form maybe formulated and configured such that start-up of delivery of drug from the controlled release composition occurs after delivery of drug from the IR component is substantially complete. Where a start-up lag time is desired, an enteric coating may be applied over the controlled release component (e.g., over a functional coating), but such a coating would necessarily limit the start-up lag to gastric residence and its associated variability. Use of enteric pore-formers would also impart a start-up lag, and such an embodiment would be more sensitive to food effects and gastric motility. Where a less pH-sensitive start-up lag time is desired, the delay may be accomplished or adjusted by the use of one or more coatings and films, including the functional coating provided over a CR core and, where utilized, the moisture barrier or cosmetic overcoats. In particular, start-up lag time as disclosed herein may be adjusted by modifying the formulation, thickness, and/or weight of the functional coating provided over the CR core, the moisture barrier layer or one or more non-functional or cosmetic overcoats.

EXAMPLES

Example 1—Controlled Release Core

A granulation used to form CR cores as described herein was manufactured in a 25 L high shear granulator according to the formula in Table 1A. Klucel EXF was divided into two equal portions; half of the Klucel EXF was dissolved in the ethanol, and half was dry blended with sodium oxybate. The material was initially granulated with 10% w/w ethanol and then titrated with another 3.5% w/w ethanol solution to achieve desired granule growth. A suitable wet mass was obtained at a total ethanol concentration of 13.5% w/w. The wet granules were divided into two sub lots and then each sub lot was dried in a 5-liter Niro fluid bed dryer. The dried granules were combined and milled through a COMIL equipped with a 14 mesh screen. Granulation parameters and particle size distribution are shown in Tables 1B and 1C, respectively.

The granulation was then combined with 2% magnesium stearate lubricant, and tablets were compressed on a 16-station press fitted with chrome-plated 0.325"×0.705" modified oval tooling. The average tablet hardness was 10.7 kiloponds.

TABLE 1A

Controlled Release Core Tablet Formulation

| | Ingredient(s) | % w/w | mg/tablet |
|---|---|---|---|
| 1 | Sodium Oxybate | 96.0 | 750.0 |
| 2 | Hydroxypropyl cellulose, NF (Klucel EXF) | 2.0 | 15.6 |
| 3 | Ethanol, USP (200 proof)* | 13.5 | |
| 4 | Magnesium Stearate, NF | 2.0 | 15.6 |
| | TOTAL | 100.0 | 781.2 |

*Granulation solvent, removed during drying step

TABLE 1B

Granulation Parameters WET GRANULATION

| | | |
|---|---|---|
| GRANULATION SOLUTION ADDITION RATE (G/MIN) | 250 | |
| TOTAL GRANULATION TIME (INCLUDING SOLUTION ADDITION AND WET MASSING TIME) | 7 MINUTES | |

TABLE 1B-continued

Granulation Parameters WET GRANULATION

| | | |
|---|---|---|
| IMPELLER SPEED (RPM) | 300 | |
| CHOPPER SPEED (RPM) | 1800 | |
| DRYING | SUBLOT 1 | SUBLOT 2 |
| DRYING INLET TEMPERATURE (° C.) | 70 | 70 |
| TOTAL DRYING TIME (MIN) | 17 | 18 |
| EXHAUST TEMPERATURE AT END OF DRYING (° C.) | 47 | 48 |
| LOD (% WT LOSS) | 0.84 | 0.92 |

TABLE 1C

Screen Analysis of Milled Granulation

| Screen size US Std mesh | Opening size microns | Wt Retained (%) |
|---|---|---|
| 20 | 850 | 2.1 |
| 40 | 420 | 10.4 |
| 60 | 250 | 19.8 |
| 80 | 180 | 25.0 |
| 120 | 125 | 22.9 |
| 200 | 75 | 12.5 |
| Pan | <45 | 7.3 |

Example 2—Functional Coating

Tablets from Example 1 were coated with a solution prepared according to the formulation in Table 2A. The ethylcellulose was first added to a 95/5 w/w mixture of ethanol and water and stirred until dissolved. Next, the hydroxypropyl cellulose and dibutyl sebacate were added and stirred until completely dissolved. 4.7 kg of tablets from Example 1 were then charged to an 8" pan Driam tablet coater and coated with the solution to 5.1 wt % gain (40 mg/tablet). The tablets were then dried for 5 minutes in the coater, and then finally cooled in the pan to an exhaust temperature below 30° C.

The dissolution profile was measured in de-ionized water using USP Apparatus 2 set to 37° C.±2° C. with paddles at 50 rpm. Samples were analyzed by HPLC. As shown in FIG. 1, the coated tablets exhibited controlled release with duration of approximately 6 hours. The dosage form released 12% of its contents after 1 hour, 34% after 2 hours, 71% after 4 hours, 93% after 6 hours, and 99% after 8 hours.

TABLE 2A

Formulation of Sodium Oxybate Sustained-Release Tablets

| | Ingredient(s) | % of coat solids | % w/w of tablet | mg/tablet |
|---|---|---|---|---|
| 5 | Sodium Oxybate tablet core | | 95.13 | 781.25 |
| 6 | Hydroxypropyl cellulose, NF (Klucel EF) | 37.0 | 1.80 | 14.80 |
| 7 | Dibutyl sebacate | 5.0 | 0.24 | 2.00 |
| 8 | Ethylcellulose, NF (Ethocel Standard Premium 10) | 58.0 | 2.82 | 23.20 |
| 9 | Ethanol, USP (200 proof)* | | | |
| 10 | Purified water* | | | |
| | TOTAL | 100.0 | 100.00 | 821.25 |

*Coating solvent, removed during processing

TABLE 2A

Coating Parameters for Driam 8" Pan Coater

| CR COATING | AVERAGE | RANGE |
|---|---|---|
| INLET TEMPERATURE (° C.) | 46 | 42-55 |
| EXHAUST TEMPERATURE (° C.) | 43 | 41-46 |
| INLET AIRFLOW (PASCAL) | >300 | >300 |
| ATOMIZATION PRESSURE (BAR) | 2 | 2.0 |
| SPRAY RATE (G/MIN) | 35 | 32-37 |
| PAN SPEED (RPM) | 6 | 5-7 |

Example 3—Immediate-Release Overcoat

A solution of 20% sodium oxybate as active and 2.0% hypromellose E-15 (HPMC E-15) as film-former was prepared in 60/40 (w/w) ethanol/water. The coating solution was manufactured by first dissolving the HPMC E15 in water, then adding the ethanol and sodium oxybate. 3 kg of 750-mg strength sustained-release tablets from Example 2 were charged to a Driam tablet coater equipped with an 8" pan and preheated to 40° C. The entire coating solution was applied according to the parameters listed in Table 3A. The tablet weight gain was monitored every 5 minutes, and the coating was stopped when the entire solution was sprayed (the theoretical weight gain is 33.5%). The tablets were dried for 15 minutes; the tablets did not lose any weight during the 15 minute drying time, and so it was assumed that the drying was complete. The tablets were then cooled in the pan to an exhaust temperature of <30° C.

Figure 2:
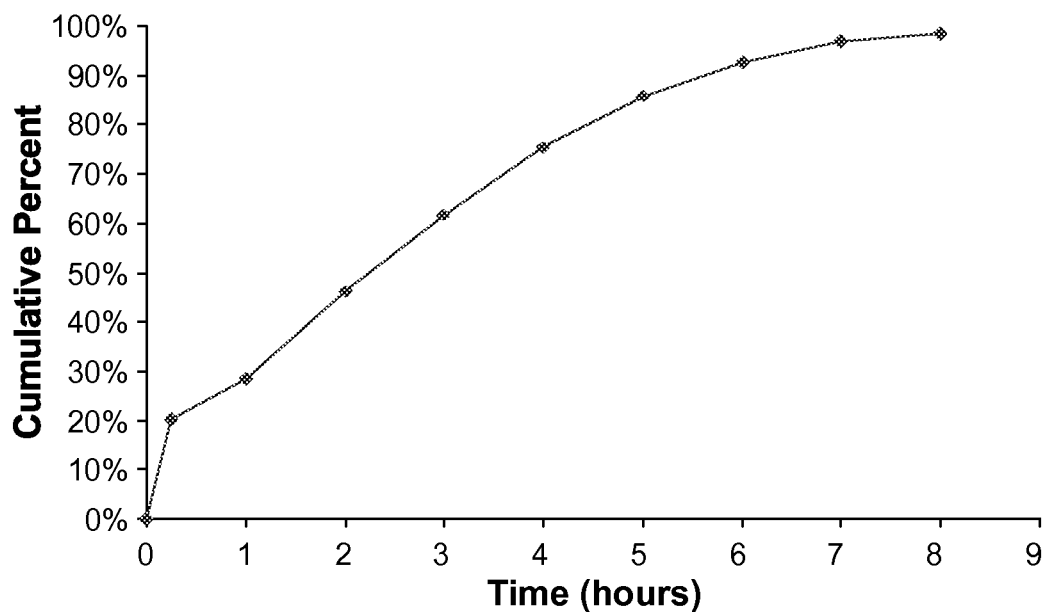
FIG. 2 shows the delivery profile of integrated dosage forms as described herein having an immediate release component and a controlled release component.
Figure 3:
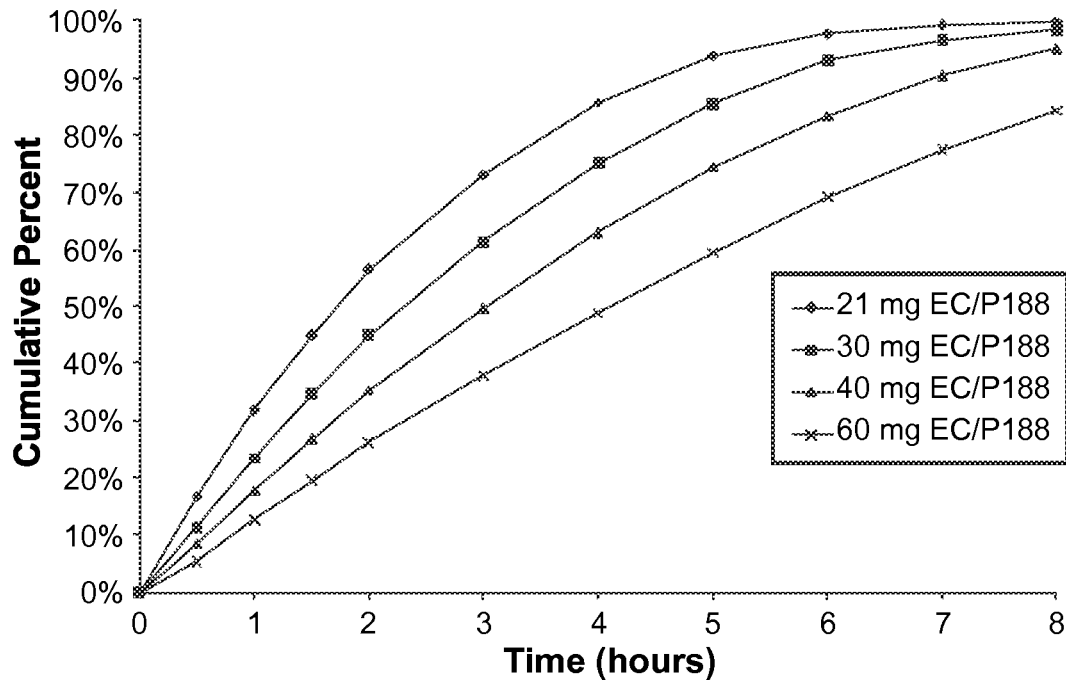
FIG. 3 provides a graph illustrating that the controlled release profile of dosage forms prepared according to the present description can be altered by altering the coating weight of a functional coating.

Analysis by HPLC revealed an overall potency of 961 mg, and thus a drug overcoat potency of 211 mg. Dissolution testing using USP Apparatus 2 set to 37° C.±2° C. with paddles at 50 rpm, shown in FIG. 2, demonstrates substantially the entire immediate-release overcoat is dissolved in 15 minutes and that controlled release is maintained for approximately 6 hours thereafter. Higher amounts of drug can be applied to the immediate release overcoat by using higher amounts of coating solution and extending the coating time accordingly.

TABLE 3A

Parameters for Immediate-Release Overcoating with 8" Driam Coater

| DRUG OVER-COATING | AVERAGE | RANGE |
|---|---|---|
| INLET TEMPERATURE (° C.) | 59 | 55-63 |
| EXHAUST TEMPERATURE (° C.) | 51 | 50-53 |
| PRODUCT TEMPERATURE (° C.) | 43 | 41-49 |
| INLET AIRFLOW (PASCAL) | >300 | >300 |
| ATOMIZATION PRESSURE (BAR) | 2 | 2 |
| SPRAY RATE (G/MIN) | 16 | 14-17 |
| PAN SPEED (RPM) | 8 | 7-8 |
| TOTAL RUN TIME (HRS) | 4 HRS 47 MIN (COATING) | |
| | 15 MIN (DRYING) | |

The following examples illustrate aspects of the sustained-release coating formulation with several evaluations using tablets from Example 1.

Example 4—Effect of Membrane Weight with Poloxamer as Pore Former in Functional Coating One means of controlling dissolution is by adjustment of the coating thickness, or amount of film applied to each tablet. This was illustrated with a film consisting of 33% poloxamer 188 (P188) and 67% ethylcellulose 10 cPs (EC-10). The coating solution was prepared by dissolving 3.59 grams of EC-10 and 1.77 grams of P188 in a mixture of 80 grams denatured alcohol ("alcohol") and 4 grams de-ionized water. (Denatured alcohol, S-L-X manufactured by W. M. Barr, is approximately a 50/50 w/w blend of methanol and ethanol.)

Twelve tablets from Example 1 were coated in a Caleva Mini-coater/Drier 2 under parameters listed in Table 4A. Periodically, the tablets were removed and weighed to determine film weight. Three tablets were removed at times corresponding to 21 mg, 30 mg, 40 mg, and finally 60 mg weight gain.

The dissolution profiles were measured with USP Apparatus 7 (Vankel Bio-dis) set to 37° C.±2° C. and using a dipping rate of 30/minute, tablets fixed in plastic holders and intervals corresponding to 0.5 h, 1 h, 1.5 h, 2 h, 3 h, 4 h, 5 h, 6 h, 7 h, 8 h, and 14 h (each interval is 50 ml volume). The tubes were analyzed by conductivity, and results are calculated as percent of total amount. The results demonstrate that controlled release is achieved with membrane weights ranging from at least 21-60 mg/tablet, and that duration of delivery increases as the membrane weight increases.

TABLE 4A

Standard Parameters for Sustained-Release Coating in Caleva Mini-Coater/Drier 2

| Parameter | Setting |
|---|---|
| Batch size | 3-12 Tablets |
| Inlet temperature | 40 C. |
| Air flow setting | 70-85% |
| Solution flow rate | 18 ml/hr |
| Agitator setting | 32 |
| Atomization pressure | 0.5 bar |
| Gun position | Adjusted to achieve desired deposition |

Figure 4:
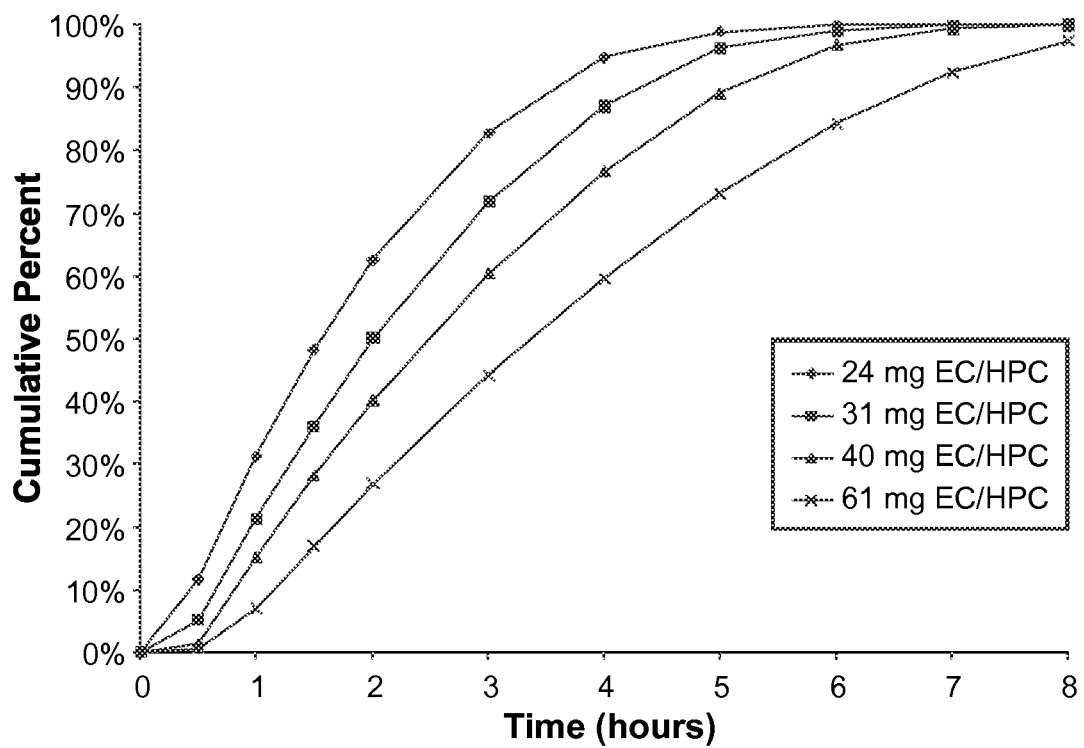
FIG. 4 provides a graph further illustrating that the controlled release profile of dosage forms prepared according to the present description can be altered by altering the coating weight of a functional coating.

Example 5—Effect of Membrane Weight with Hydroxypropyl Cellulose as Pore Former in Functional Coating Following procedures of Example 4, 12 tablets from Example 1 were coated with a film consisting of 36.5% HPC-EF, 5.0% dibutyl sebacate (DBS), and 58.5% EC-10 (all percentages by weight) coated from a solution consisting of 7% solids in 95/5 alcohol/water. The results shown in FIG. 4 demonstrate that controlled release over a relevant time period is achieved with membrane weights ranging from at least 21-60 mg/tablet, and that duration of delivery increases as the membrane weight increases.

Example 6—Effect of Poloxamer Level in Functional Coating

Figure 5:
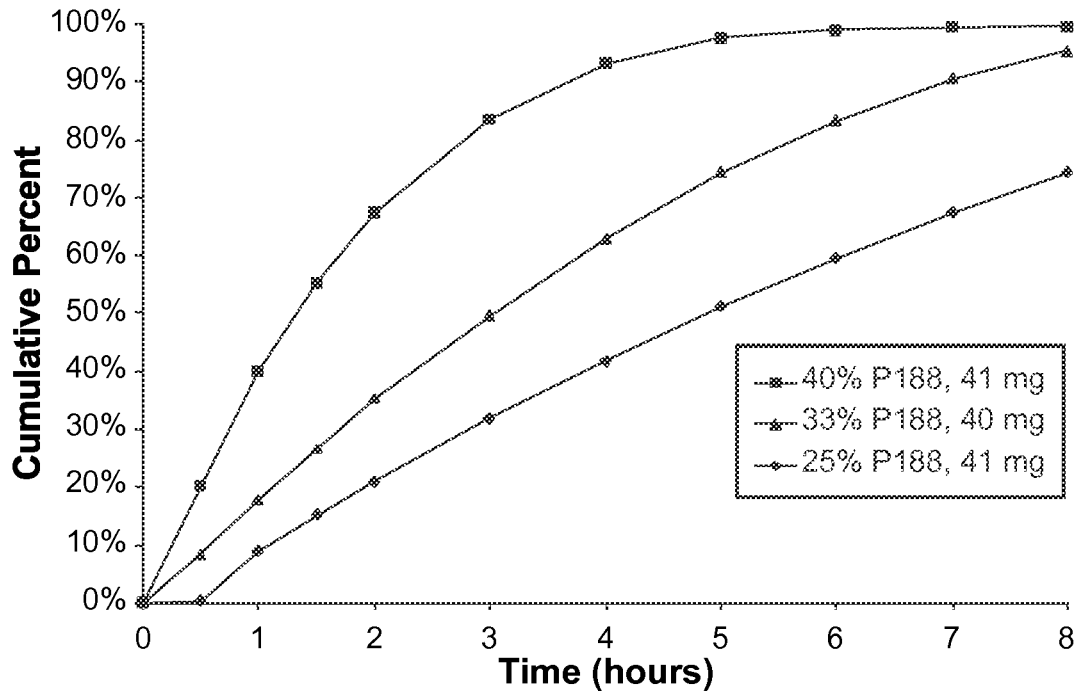
FIG. 5 provides a graph illustrating that the controlled release profile of dosage forms prepared according to the present description can be altered by altering the amount of pore former included within a functional coating.

In addition to adjustment of membrane weight, another useful means of controlling release rate or duration is by adjustment of the pore-former content of the formulation. Following procedures of Example 4, two additional solutions consisting of (a) 25% P188 by weight/75% EC-10 by weight and (b) 40% P188 by weight/60% EC-10 by weight were prepared as 7% (w/w) solutions in 95/5 alcohol/water. In each of the two separate coatings, four tablets from Example 1 were coated to 41 mg. The dissolution profiles are shown in FIG. 5, along with that of the 40 mg set of Example 4 for comparison. The results demonstrate that poloxamer level can be adjusted at least over the range of 25%-40% by weight, while still providing controlled release of the drug.

Example 7—Effect of Hydroxypropyl Cellulose Level in Functional Coating

Figure 6:
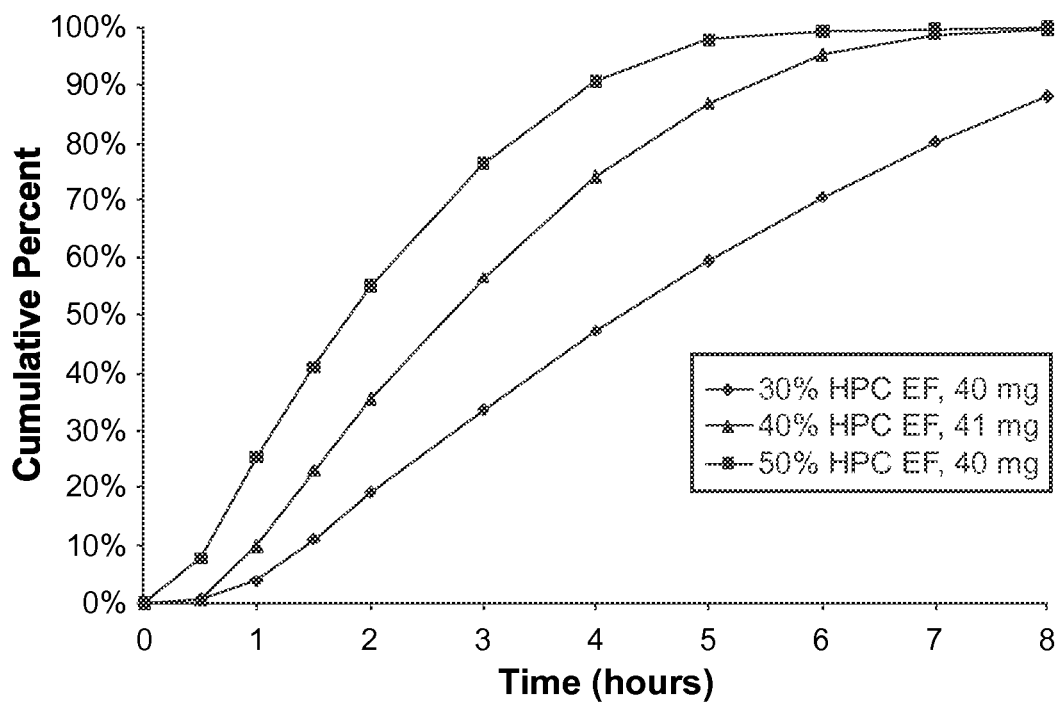
FIG. 6 provides a graph further illustrating that the controlled release profile of dosage forms prepared according to the present description can be altered by altering the amount of pore former included within a functional coating.

In a fashion similar to Example 6, the effect of HPC level in the functional coating was evaluated over the range of 30%-50% by weight. Three separate coating solutions were prepared with 30%, 40%, and 50% HPC-EF; 5% DBS; and the balance EC-10. All solutions were prepared with 7% total components in 95/5 alcohol/water. In each coating, 4 tablets from Example 1 were coated to 40-41 mg/tablet weight gain. The dissolution profiles shown in FIG. 6 demonstrate controlled release of the drug was achieved with HPC levels of at least 30-50% by weight.

Figure 7:
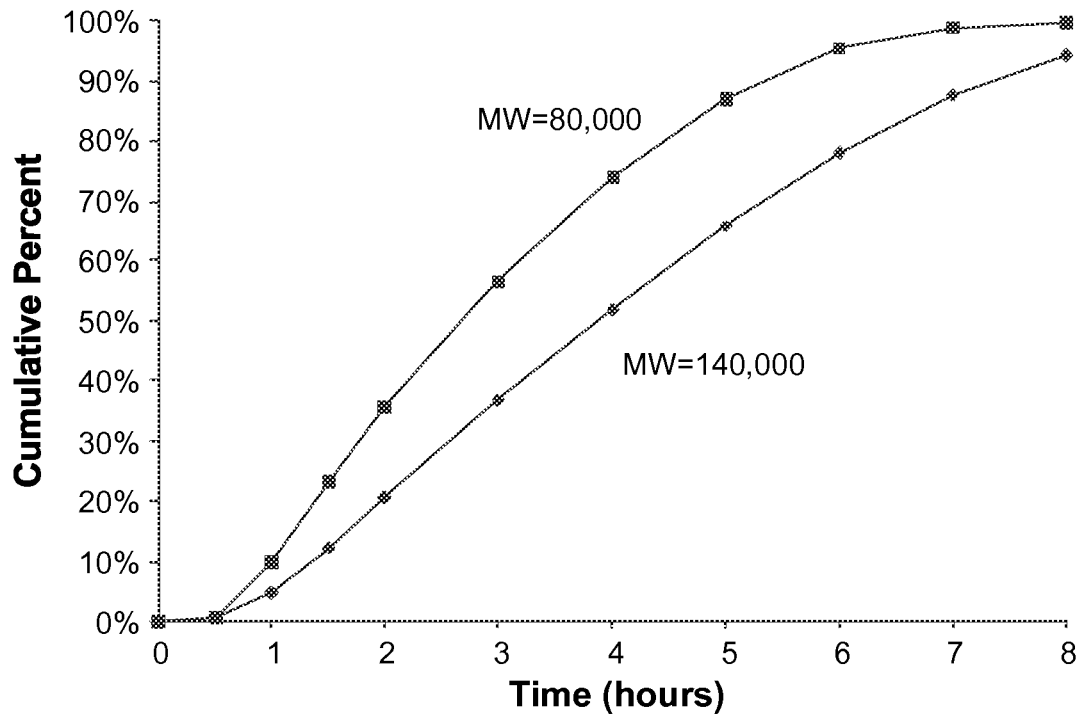
FIG. 7 provides a graph illustrating that the controlled release profile of dosage forms prepared according to the present description can be altered by varying the molecular weight of a pore former included within a functional coating.

Example 8—Effect of Hydroxypropyl Cellulose Molecular Weight when Used in Functional Coating Hydroxypropyl cellulose is supplied in several molecular weight grades, many of which may be suitable for use as pore-formers in ethylcellulose films. Two such grades (Klucel "EF" and "JF", supplied by Ashland) corresponding to 80,000 daltons and 140,000 daltons were evaluated with other components fixed. Following procedures of Example 4, solutions were prepared with 40% HPC, 5% DBS, and 55% EC-10 (all percentages by weight) using 7% total components in 95/5 alcohol/water. In each coating, 4 tablets from Example 1 were coated to 40-41 mg/tablet weight gain. The results shown in FIG. 7 demonstrate a modest effect of molecular weight and that the two grades tested provide for acceptable release profiles.

Example 9—Effect of Ethylcellulose Molecular Weight or Viscosity

Figure 8:
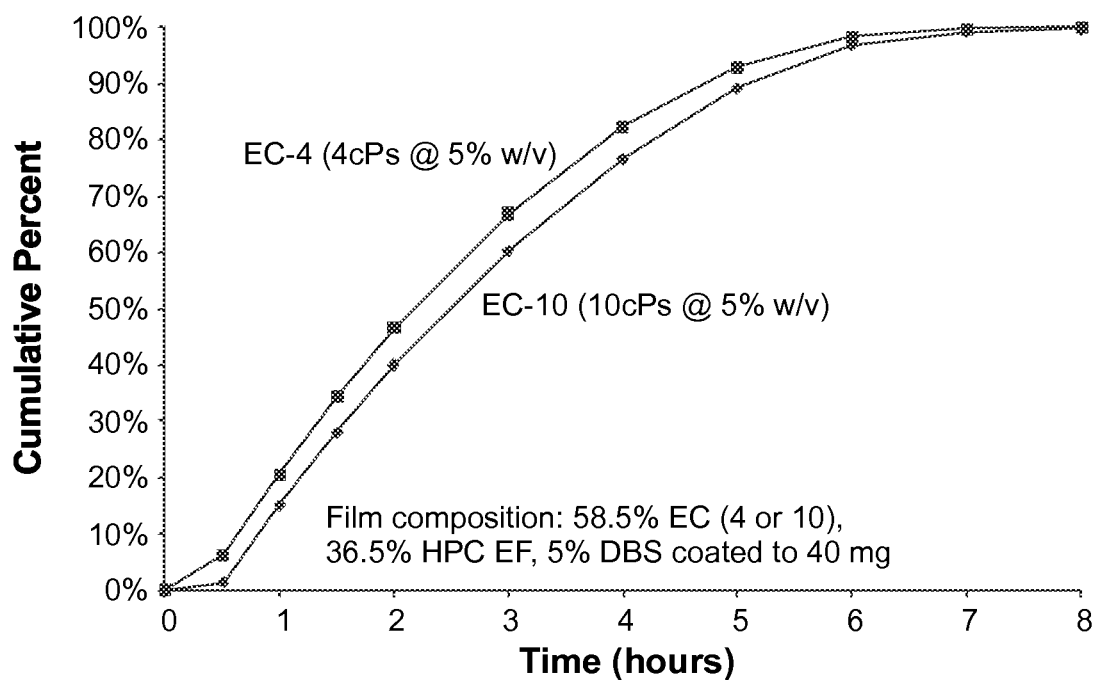
FIG. 8 provides a graph illustrating that suitable controlled release profiles from dosage forms prepared according to the present description can be achieved even with functional coatings formed using different grades of the same base polymer material.

Another consideration is the molecular weight, or viscosity, of ethylcellulose. Two grades were evaluated, corresponding to 4 cPs and 10 cPs viscosity for a 5% solution. Following procedures of Example 4, two solutions were prepared corresponding to 58.5 wt % ethylcellulose (EC-4 or EC-10), 36.5 wt % HPC-EF, and 5.0 wt % DBS having 7% w/w total components in 95/5 alcohol/water. Tablets from Example 1 were coated to 40 mg/tablet weight gain, and dissolution profiles are shown as FIG. 8. The results indicate both grades of ethylcellulose provide for acceptable profiles, and suggest that other ethylcellulose grades (such as 20 cPs) may also be acceptable.

Example 10—Demonstration of Alcohol Ruggedness of Controlled Release Sodium Oxybate Tablets Co-administration of sustained-release dosage forms with alcoholic beverages is a relevant concern, as ethanol is known to dissolve certain rate-controlling components that would not otherwise be dissolved. In some dosage forms, this may lead to dose-dumping. As ethanol is rapidly absorbed in the stomach, a relevant test involves dissolution of the dosage form in vodka (40% ethanol nominal) for 2 hours (representing gastric retention time), followed by normal dissolution in de-ionized water.

Figure 9A:
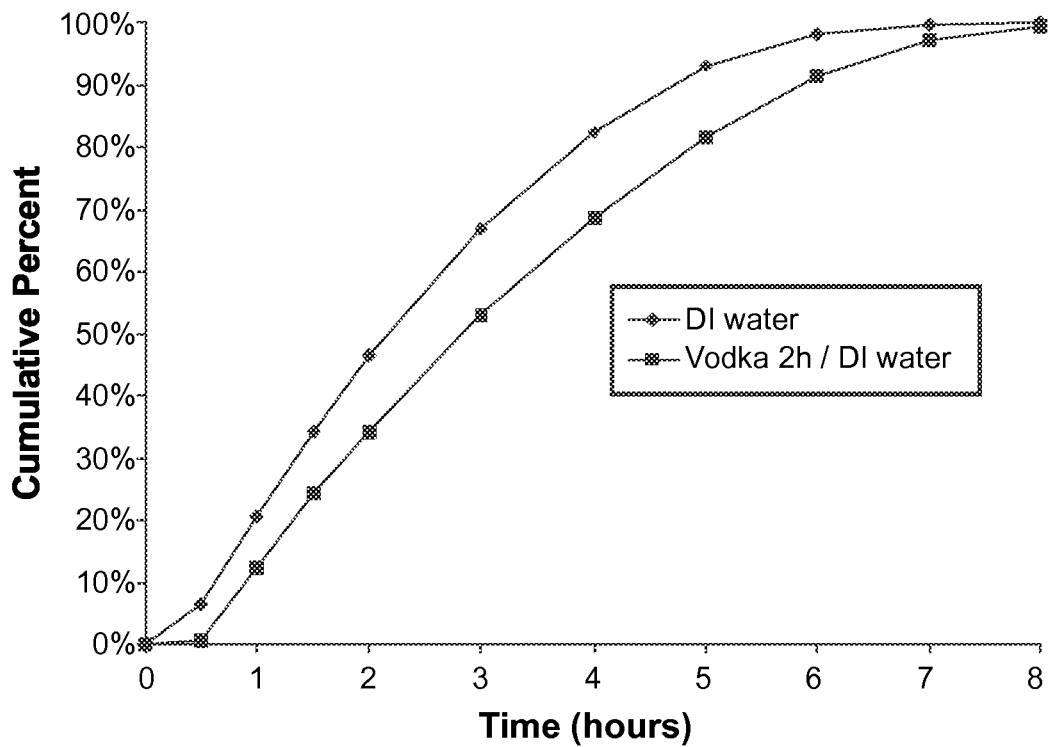
FIG. 9A and FIG. 9B provide graphs illustrating the effects of alcohol on the delivery profile of sustained-release formulations prepared as described herein.

This test was performed on sustained-release tablets from Example 9 (36.5 wt % HPC EF, 5 wt % DBS, 58.5 wt % EC-4). The analysis of sodium oxybate by conductivity was corrected for the different response in vodka vs. de-ionized water. The results shown in FIG. 9A indicate that dissolution is slower in Vodka, and that no dose-dumping occurred.

Figure 9B:
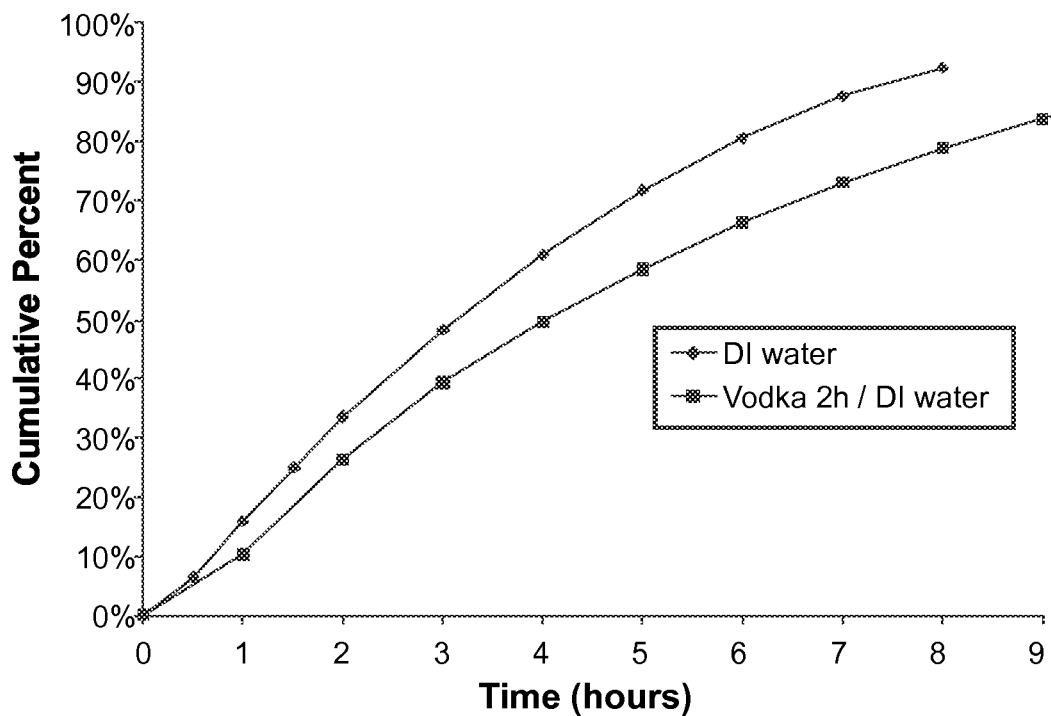

Likewise, a similar test was performed on sustained-release tablets with a film comprised of 33 wt % P188 and 67 wt % EC-10. Those results, shown in FIG. 9B, also indicate slower release in vodka and no dose-dumping.

Example 11—Aqueous Coating of Controlled Release Film

Figure 10:
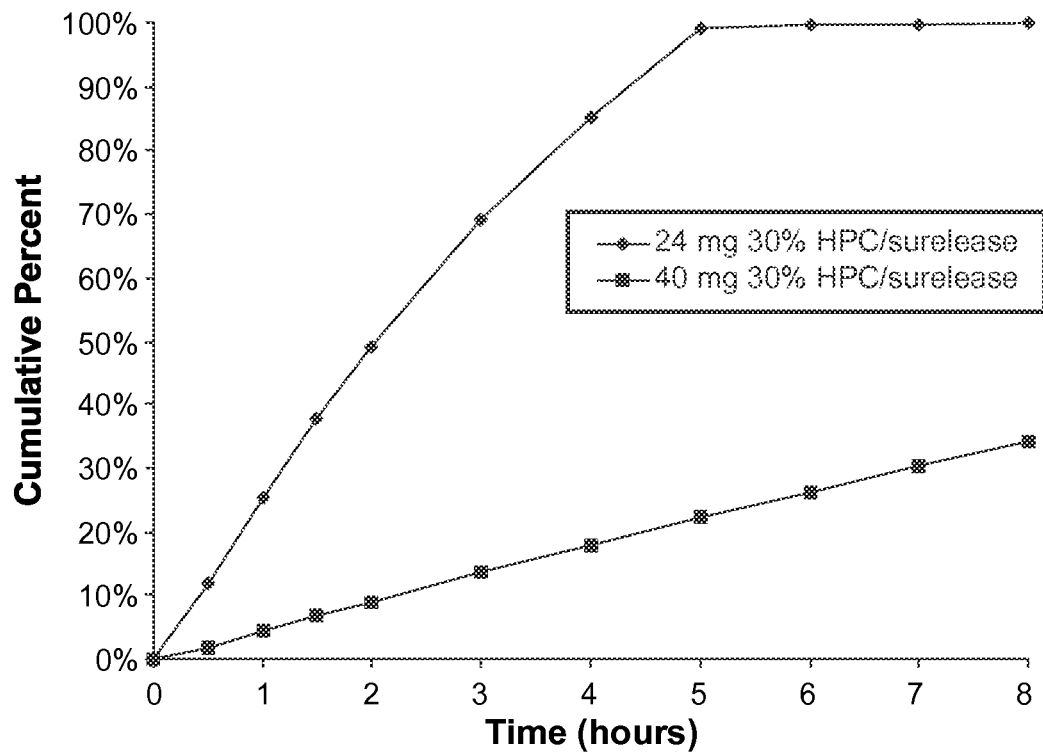
FIG. 10 provides a graph illustrating the controlled release performance achieved by dosage forms as described herein having functional coatings prepared from aqueous dispersions of ethylcellulose as the base polymer.

Due to the hygroscopic nature of sodium oxybate, coating the rate-controlling film from an alcoholic solution is desirable. However, use of ethylcellulose aqueous dispersions is attractive for environmental and cost considerations. A film consisting of 30 wt % HPC EF and 70 wt % Surelease (aqueous ethylcellulose dispersion) was deposited on tablets from Example 1 as follows. First, 1.37 grams of HPC EF was dissolved in 22.6 grams de-ionized water. This was then poured into 32.5 grams of Surelease E-7-19040-clear while stirring. Eight tablets were coated in the Caleva Mini-coater/Drier 2 with flow rate of 15 ml/hr and 58° C. inlet temperature. Samples removed at 24 mg and 40 mg were then tested for dissolution, with no post-coating heat treatment. The results are shown in FIG. 10.

Example 12—Calcium Oxybate Controlled Release

Figure 11:
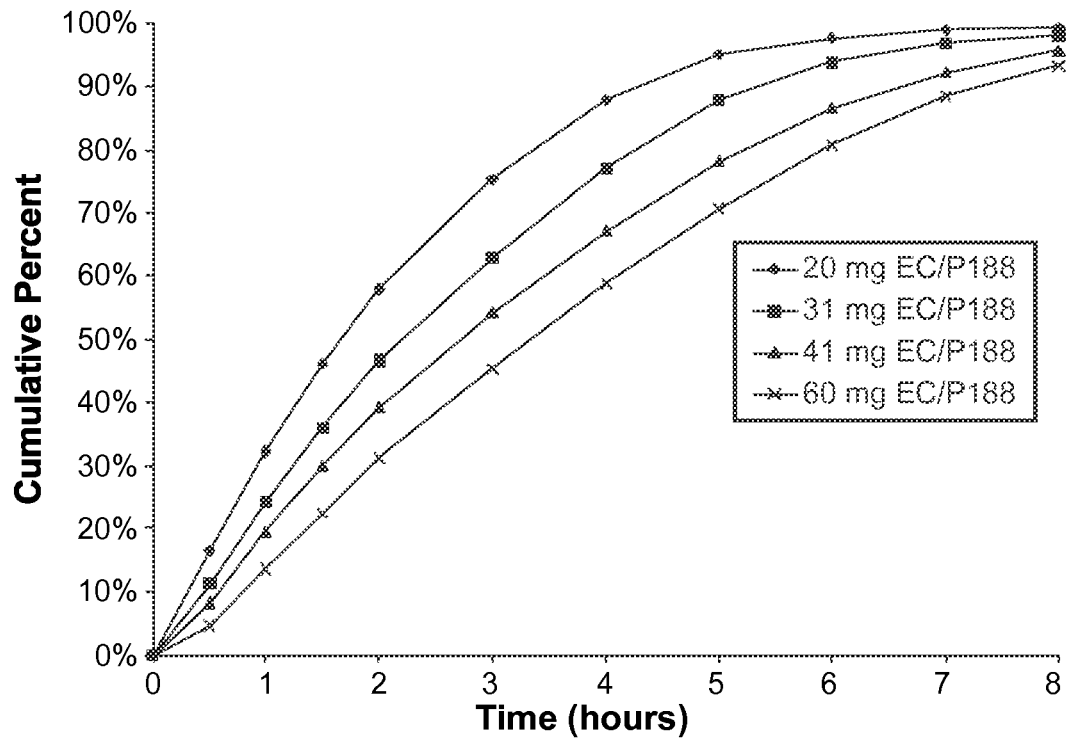
FIG. 11 provides a graph illustrating the controlled release performance achieved by dosage forms as described herein incorporating calcium oxybate as the drug.

A controlled release dosage form for delivery of calcium oxybate was prepared by generally following procedures of Example 1 found in U.S. Pat. No. 4,393,296 (Klosa, Production of Nonhygroscopic Salts of 4-Hydroxybutyric Acid). The isolated calcium oxybate was milled to pass through a 16-mesh screen. For this study, a small sample comprising 9.3 grams of calcium oxybate was blended with 0.19 grams of sodium stearyl fumarate (Pruv, JRS Pharma, Rosenberg, Germany). 800 mg aliquots of this 98% calcium oxybate and 2% sodium stearyl fumarate were then directly compressed into tablets using 0.325"×0.705" modified oval tooling and a Carver press with 1-ton applied force. Following procedures of Example 4, nine tablets were coated with a film having 33% poloxamer 188 and 67% EC-10 from a solution of 7% w/w solids in 95/5 alcohol/water. Two tablets were removed at each intermediate coating weight corresponding to 20 mg, 32 mg, 41 mg, and finally at 60 mg. The dissolution profiles are shown as FIG. 11. These results using calcium oxybate follow the general behavior of sodium oxybate demonstrated in Example 4.

Example 13—Clinical Evaluation of Controlled Release Dosage Forms

An open-ended, randomized, crossover study was conducted to evaluate controlled release dosage forms as described herein. The controlled release dosage forms were formulated to deliver sodium oxybate and were compared to a sodium oxybate oral solution (commercially available as Xyrem® (sodium oxybate) oral solution). The study was conducted in healthy male and female volunteers.

Four different sodium oxybate formulations were administered to patients. The first, designated herein as Treatment A, was the sodium oxybate oral solution containing 375 mg/ml sodium oxybate. Treatments B through E, as designated herein, involved administration of three controlled release dosage forms (Treatments B through D), with one of the controlled release dosage forms being used to administer two different doses of sodium oxybate (Treatments D and E). The controlled release dosage forms administered as Treatment B included 750 mg sodium oxybate per dosage form and were produced with a CR core and functional overcoat as described in Example 1 and Example 2, the controlled release dosage forms administered as Treatment C included 750 mg sodium oxybate per dosage form and were produced as described in Example 1 and Example 4, and the controlled release dosage forms administered as Treatments D and E included 1,000 mg sodium oxybate per dosage form and were produced with a CR core (750 mg sodium oxybate), functional overcoat, and IR overcoat (250 mg sodium oxybate) as described in Examples 1 through 3.

Figure 12:
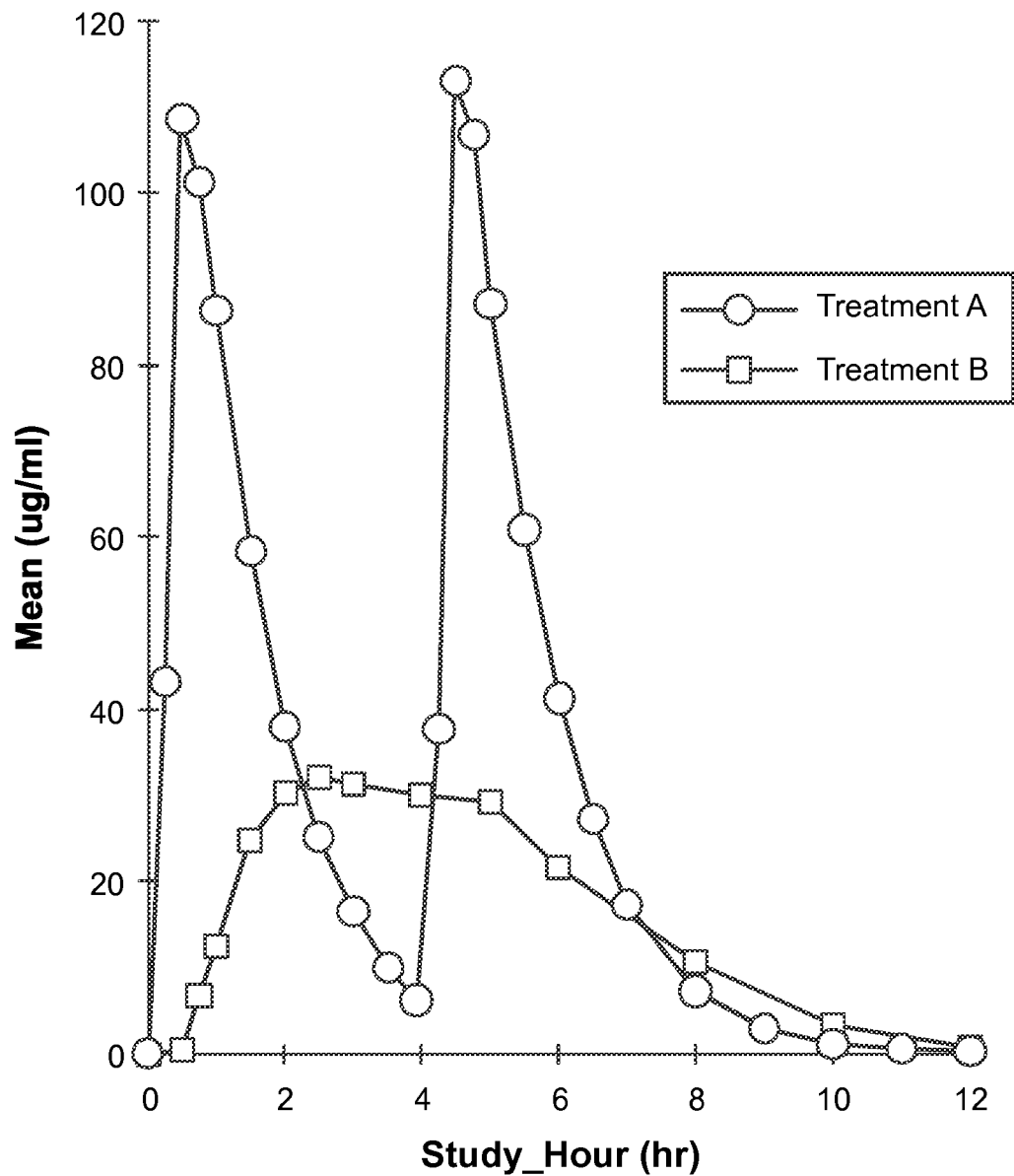
FIG. 12 provides a graph illustrating the plasma concentration of sodium oxybate over time provided by a sodium oxybate oral solution (Treatment A) and a sodium oxybate controlled release dosage form as described herein (Treatment B).
Figure 13:
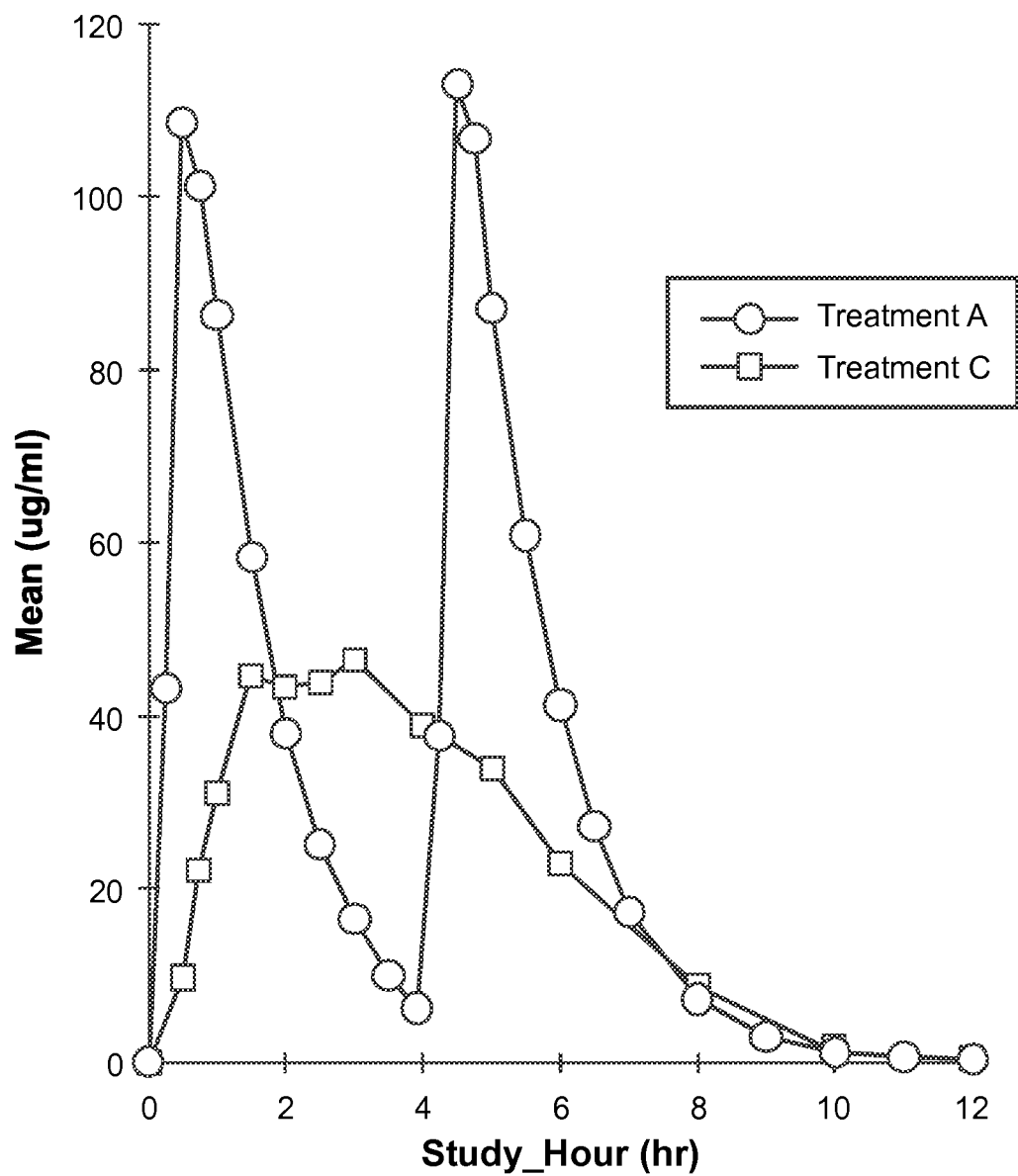
FIG. 13 provides a graph illustrating the plasma concentration of sodium oxybate over time provided by a sodium oxybate oral solution (Treatment A) and a sodium oxybate controlled release dosage form as described herein (Treatment C).

Patients were divided into two groups. The first group received Treatment A, Treatment B, and Treatment C over the course of the clinical study, with a washout period between each treatment. Treatment A was administered to each patient as two 3 g doses given four hours apart (one dose at time zero and the second dose four hours later), for a total dose of 6 g sodium oxybate. Treatments B and C were administered to each patient only at time zero, with each treatment being administered as 8 tablets, providing a total dose of 6 g sodium oxybate. Blood samples from each patient were taken at various intervals and analyzed by LC/MS for total sodium oxybate content in the plasma. A total of 29 patients received Treatment A, a total of 19 patients received Treatment B, and a total of 19 patients received Treatment C. The mean plasma concentration of sodium oxybate over time achieved by each of the treatments is shown in FIG. 12 (Treatment A and Treatment B) and FIG. 13 (Treatment A and Treatment C), and a summary of pharmacokinetic parameters provided by Treatments A through C are provided in Table 5.

TABLE 5

Summary of PK Parameters for Treatments A, B, C

| | $\lambda\_z$ (1/hr) | $T_{1/2}$ (hr) | Tmax (hr) [a] | Cmax (ug/ml) | AUClast (hr * ug/ml) | AUCinf (hr * ug/ml) |
|---|---|---|---|---|---|---|
| Treatment A | | | | | | |
| N | 29 | 29 | 29 | 29 | 29 | 29 |
| Mean | 1.22 | 0.60 | 4.50 (0.5, 4.75) | 130.79 | 350.84 | 351.20 |
| SD | 0.27 | 0.13 | | 31.52 | 116.74 | 116.74 |
| CV % | 21.93 | 22.61 | | 24.10 | 33.27 | 33.24 |
| Mean | 1.19 | 0.58 | | 127.37 | 333.33 | 333.72 |
| Treatment B | | | | | | |
| N | 18 | 18 | 19 | 19 | 19 | 18 |
| Mean | 0.62 | 1.22 | 2.00 (1.50, 5.00) | 41.78 | 188.23 | 196.25 |
| SD | 0.16 | 0.40 | | 18.40 | 103.60 | 102.50 |
| CV % | 26.44 | 32.58 | | 44.03 | 55.04 | 52.23 |
| Mean | 0.59 | 1.17 | | 38.46 | 163.80 | 173.33 |
| Treatment C | | | | | | |
| N | 19 | 19 | 19 | 19 | 19 | 19 |
| Mean | 0.74 | 0.99 | 2.50 (1.00, 5.00) | 50.49 | 221.64 | 222.60 |
| SD | 0.16 | 0.23 | | 15.83 | 106.85 | 106.80 |
| CV % | 22.25 | 22.93 | | 31.35 | 48.21 | 47.98 |
| Mean | 0.72 | 0.96 | | 48.10 | 200.08 | 201.12 |

Figure 14:
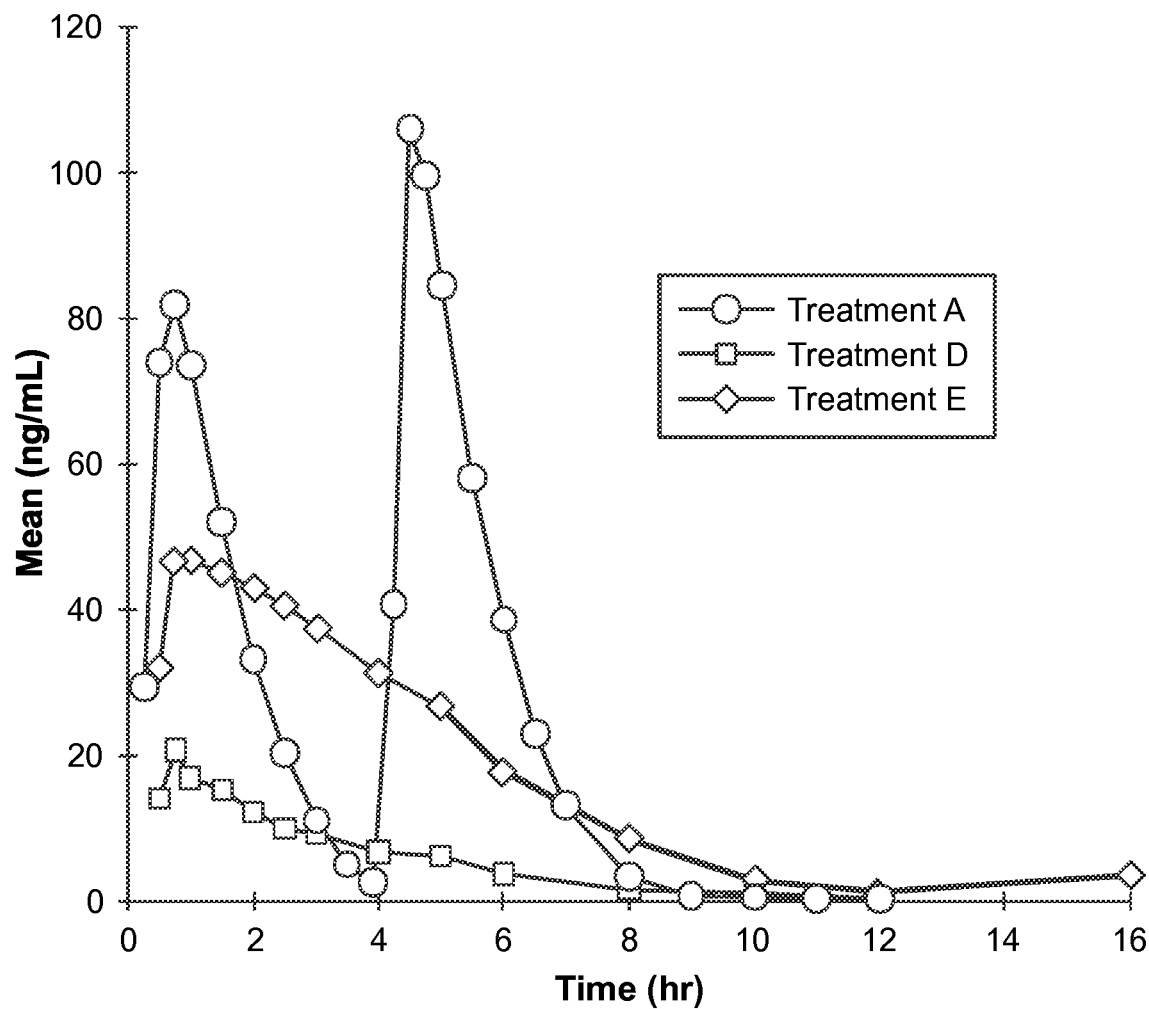
FIG. 14. provides a graph illustrating the plasma concentration of sodium oxybate over time provided by a sodium oxybate oral solution (Treatment A) and a sodium oxybate controlled release dosage form as described herein dosed at 4 g (Treatment D) and 8 g (Treatment E).

The second group was administered Treatment A, Treatment D, and Treatment E during over the course of the clinical study, with a washout period between each treatment. Again, Treatment A was administered to each patient as two 3 g doses given four hours apart (one dose at time zero and the second dose four hours later), for a total dose of 6 g sodium oxybate. Treatments D and E were administered to each patient only at time zero. Patients receiving Treatment D were administered 4 tablets at time zero, providing a total dose of 4 g sodium oxybate, and patients receiving Treatment E were administered 8 tablets at time zero, providing a total dose of 8 g sodium oxybate. Blood samples from each patient were taken at various intervals and analyzed by LC/MS for total sodium oxybate content in the plasma. A total of 30 patients received Treatment A, and a total of 30 patients received Treatments D and E. The mean plasma concentration of sodium oxybate over time achieved by each of the treatments is shown in FIG. 14, and a summary of pharmacokinetic parameters provided by Treatments A through C are provided in Table 6.

TABLE 6

Summary of PK Parameters for Treatments A, D, E

| | $\lambda\_z$ (1/hr) | $T_{1/2}$ (hr) | Tmax (hr) [a] | Cmax (ug/ml) | AUClast (hr * ug/ml) | AUCinf (hr * ug/ml) |
|---|---|---|---|---|---|---|
| Treatment A | | | | | | |
| N | 30 | 30 | 30 | 30 | 30 | 30 |
| Mean | 1.08 | 0.71 | 4.50 (0.50, 5.50) | 114.59 | 301.28 | 301.59 |
| SD | 0.31 | 0.27 | | 27.91 | 100.85 | 100.87 |
| CV % | 29.00 | 37.90 | | 24.36 | 33.47 | 33.45 |
| Mean | 1.03 | 0.67 | | 111.20 | 285.47 | 285.79 |
| Treatment D | | | | | | |
| N | 30 | 30 | 30 | 30 | 30 | 30 |
| Mean | 0.46 | 1.63 | 0.75 (0.50, 2.50) | 25.10 | 64.44 | 65.58 |
| SD | 0.14 | 0.47 | | 7.33 | 20.36 | 20.26 |
| CV % | 30.27 | 29.00 | | 29.20 | 31.60 | 30.90 |
| Mean | 0.44 | 1.56 | | 24.01 | 61.31 | 62.55 |
| Treatment E | | | | | | |
| N | 30 | 30 | 30 | 30 | 30 | 30 |
| Mean | 0.59 | 1.36 | 1.00 (0.50, 5.00) | 59.52 | 242.30 | 243.80 |
| SD | 0.20 | 0.64 | | 17.72 | 117.15 | 116.79 |
| CV % | 34.57 | 46.91 | | 29.77 | 48.35 | 47.91 |
| Mean | 0.55 | 1.25 | | 56.89 | 216.33 | 218.12 |

[a] Tmax is summarized as median (min, max).

It will be obvious to those having skill in the art that many changes may be made to the details of the above-described embodiments without departing from the underlying principles of the invention. The scope of the present invention should, therefore, be determined only by the following claims.

The invention claimed is:

1. A formulation comprising a sustained release portion comprising about 500 mg to 12 g of at least one pharmaceutically active ingredient selected from gamma-hydroxybutyrate and pharmaceutically acceptable salts of gamma-hydroxybutyrate, wherein:

the sustained release portion comprises a functional coating and a core, the functional coating is deposited over the core;

the core comprises at least one pharmaceutically active ingredient selected from gamma-hydroxybutyrate and pharmaceutically acceptable salts of gamma-hydroxybutyrate;

the functional coating comprises one or more methacrylic acid-methyl methacrylate co-polymers that are from about 20% to about 50% by weight of the functional coating; and the sustained release portion releases greater than about 40% of its gamma-hydroxybutyrate by about 4 to about 6 hours when tested in a dissolution apparatus 2 in deionized water at a temperature of 37° C. and a paddle speed of 50 rpm.

2. The formulation of claim 1, wherein the sustained release portion releases about 60% to about 90% of its gamma-hydroxybutyrate by about 6 hours when tested in a dissolution apparatus 2 in deionized water at a temperature of 37° C. and a paddle speed of 50 rpm.

3. The formulation of claim 1, wherein the sustained release portion releases about 10% or less of its gamma-hydroxybutyrate by about 1 hour when tested in a dissolution apparatus 2 in deionized water at a temperature of 37° C. and a paddle speed of 50 rpm.

4. The formulation of claim 1, wherein the sustained release portion comprises hydrogenated vegetable oil, hydrogenated castor oil, or mixtures thereof.

5. The formulation of claim 1, comprising a calcium, lithium, potassium, sodium or magnesium salt of gamma-hydroxybutyrate or mixtures thereof.

6. The formulation of claim 5, comprising a sodium salt of gamma-hydroxybutyrate.

7. The formulation of claim 1, wherein the one or more methacrylic acid-methyl methacrylate co-polymers comprise from about 30% to about 45% by weight of the functional coating.

8. The formulation of claim 1, further comprising an immediate release portion comprising at least one pharmaceutically active ingredient selected from gamma-hydroxybutyrate and pharmaceutically acceptable salts of gamma-hydroxybutyrate.

9. The formulation of claim 8, wherein the immediate release portion comprises a calcium, lithium, potassium, sodium or magnesium salt of gamma-hydroxybutyrate or mixtures thereof.

10. The formulation of claim 9, wherein the immediate release portion comprises a sodium salt of gamma-hydroxybutyrate.

11. The formulation of claim 8, wherein the immediate release portion is a dry powder formulation, an immediate release tablet, an encapsulated formulation, a liquid solution, or liquid suspension.

12. The formulation of claim 8, wherein the immediate release portion comprises about 55 mg to 12 g of at least one pharmaceutically active ingredient selected from gamma-hydroxybutyrate and pharmaceutically acceptable salts of gamma-hydroxybutyrate.

13. The formulation of claim 8, wherein the formulation releases at least about 30% of its gamma-hydroxybutyrate by one hour when tested in a dissolution apparatus 2 in deionized water at a temperature of 37° C. and a paddle speed of 50 rpm; and greater than about 90% of its gamma-hydroxybutyrate by 8 hours when tested in a dissolution apparatus 2 in deionized water at a temperature of 37° C. and a paddle speed of 50 rpm.

14. The formulation of claim 13, wherein the formulation releases greater than about 90% of its gamma-hydroxybutyrate by 7 hours when tested in a dissolution apparatus 2 in deionized water at a temperature of 37° C. and a paddle speed of 50 rpm.

15. The formulation of claim 13, wherein the formulation releases greater than about 90% of its gamma-hydroxybutyrate by 6 hours when tested in a dissolution apparatus 2 in deionized water at a temperature of 37° C. and a paddle speed of 50 rpm.

* * * * *